US012788435B2

(12) United States Patent
Kaufmann et al.

(10) Patent No.: US 12,788,435 B2
(45) Date of Patent: Nov. 10, 2026

(54) SYSTEMS AND METHODS FOR MANIPULATION OF PERIMODIOLAR ELECTRODE ARRAYS

(71) Applicant: IotaMotion, Inc., Iowa City, IA (US)

(72) Inventors: Christopher Kaufmann, Iowa City, IA (US); Parker Reineke, North Liberty, IA (US)

(73) Assignee: IotaMotion, Inc., St. Paul, MN (US)

( * ) Notice: Subject to any disclaimer, the term of this patent is extended or adjusted under 35 U.S.C. 154(b) by 492 days.

(21) Appl. No.: 18/336,448

(22) Filed: Jun. 16, 2023

(65) Prior Publication Data

US 2023/0320751 A1 Oct. 12, 2023

Related U.S. Application Data

(63) Continuation-in-part of application No. 17/180,087, filed on Feb. 19, 2021, now Pat. No. 12,042,173, (Continued)

(51) Int. Cl.
*A61B 17/34* (2006.01)
*A61B 34/30* (2016.01)
(Continued)

(52) U.S. Cl.
CPC .......... *A61B 17/3468* (2013.01); *A61B 34/30* (2016.02); *A61N 1/36038* (2017.08); (Continued)

(58) Field of Classification Search
CPC .............. A61B 17/22; A61B 17/00234; A61B 17/3468; A61B 2034/301; (Continued)

(56) References Cited

U.S. PATENT DOCUMENTS 3,610,877 A * 10/1971 Driscoll ............. B23K 35/0205 219/68
4,383,532 A 5/1983 Dickhudt
(Continued)

FOREIGN PATENT DOCUMENTS

AU 2016323477 B2 3/2017
AU 2021232688 A1 10/2021
(Continued)

OTHER PUBLICATIONS

"U.S. Appl. No. 15/759,643, Advisory Action mailed Jun. 8, 2021", 3 pgs.

(Continued)

*Primary Examiner* — Phong Son H Dang
(74) *Attorney, Agent, or Firm* — Schwegman Lundberg & Woessner. P.A.

(57) ABSTRACT

A system for robotically assisted manipulation of an elongate implant such as a cochlear implant and related implantation sheath is discussed herein. The system can include a main enclosure housing a first actuator to control linear movement of a sheath and second actuator to control linear movement of the elongate implant. The system can also include a drive head including a first drive structure to transmit actuation generated by the first actuator to the sheath and a second drive structure to transmit actuation generated by the second actuator to the elongate implant.

15 Claims, 18 Drawing Sheets

Related U.S. Application Data which is a continuation of application No. 16/926,335, filed on Jul. 10, 2020, now Pat. No. 10,945,761, which is a continuation-in-part of application No. 16/486,030, filed as application No. PCT/US2018/018182 on Feb. 14, 2018, now Pat. No. 10,987,513, said application No. 16/926,335 is a continuation-in-part of application No. PCT/US2019/020130, filed on Feb. 28, 2019.

(60) Provisional application No. 63/353,364, filed on Jun. 17, 2022, provisional application No. 62/872,625, filed on Jul. 10, 2019, provisional application No. 62/640,964, filed on Mar. 9, 2018, provisional application No. 62/573,487, filed on Oct. 17, 2017, provisional application No. 62/458,846, filed on Feb. 14, 2017.

(51) Int. Cl.
*A61N 1/36* (2006.01)
*A61N 1/372* (2006.01)
*A61B 17/00* (2006.01)

(52) U.S. Cl.
CPC .... *A61N 1/372* (2013.01); *A61B 2017/00398* (2013.01); *A61B 2017/00477* (2013.01)

(58) Field of Classification Search
CPC .... A61B 2217/005; A61B 2017/00238; A61B 2017/00305; A61B 2017/00367; A61B 2017/00398; A61B 2017/00477; A61B 2017/22079; A61B 2017/22084; A61F 2/00; A61F 2/01; A61F 2/04; A61F 2/24
See application file for complete search history.

(56) References Cited

U.S. PATENT DOCUMENTS 4,532,930 A 8/1985 Crosby et al.
4,637,404 A * 1/1987 Gessman ............... A61N 1/056 607/126
5,197,982 A 3/1993 Goldsmith, III et al.
5,201,765 A 4/1993 Netterville et al.
5,306,298 A 4/1994 Godley, III et al.
5,593,439 A 1/1997 Cummings et al.
5,758,396 A 6/1998 Jeon et al.
6,497,645 B1 12/2002 Halpern
7,524,320 B2 4/2009 Tierney et al.
7,691,098 B2 4/2010 Wallace et al.
8,010,210 B2 * 8/2011 Rau .......................... A61B 5/06 607/137
8,229,574 B2 7/2012 Parker et al.
8,583,261 B2 11/2013 Llinas et al.
8,594,799 B2 11/2013 Haller et al.
8,886,331 B2 11/2014 Labadie et al.
9,675,446 B2 6/2017 Jaber et al.
9,700,408 B1 7/2017 Sataloff
9,986,998 B2 6/2018 Martin et al.
10,085,806 B2 10/2018 Hagn et al.
10,575,951 B2 * 3/2020 Johnson ................ A61F 2/2418
10,945,761 B2 3/2021 Kaufmann et al.
10,987,513 B2 4/2021 Kaufmann et al.
11,167,137 B2 11/2021 Kaufmann et al.
11,241,576 B2 2/2022 Hansen et al.
12,011,594 B2 6/2024 Kaufmann et al.
12,042,173 B2 7/2024 Kaufmann et al.
12,311,173 B2 5/2025 Kaufmann et al.
12,558,123 B2 2/2026 Kaufmann et al.
12,611,298 B2 * 4/2026 Oba ...................... A61F 2/2409
2001/0014818 A1 8/2001 Kennedy
2002/0065480 A1 5/2002 Hofmann
2003/0171758 A1 * 9/2003 Gibson .............. A61B 17/3468 607/57
2003/0171787 A1 9/2003 Money et al.
2004/0236390 A1 * 11/2004 Dadd ................... A61N 1/0541 607/137
2005/0004627 A1 * 1/2005 Gibson ................ A61N 1/0529 607/57
2005/0245991 A1 * 11/2005 Faltys ................ A61N 1/36038 607/57
2006/0047318 A1 3/2006 Pastore et al.
2006/0241723 A1 * 10/2006 Dadd ...................... A61F 11/00 607/57
2007/0156123 A1 7/2007 Moll et al.
2007/0225787 A1 9/2007 Simaan et al.
2008/0077221 A1 3/2008 Milojevic et al.
2008/0188931 A1 8/2008 Kwon
2010/0114288 A1 5/2010 Haller et al.
2010/0145138 A1 6/2010 Forsell
2010/0145143 A1 6/2010 Salomon et al.
2011/0021903 A1 * 1/2011 Strommer .............. A61B 5/367 607/9
2011/0066160 A1 3/2011 Simaan et al.
2011/0106101 A1 5/2011 Tortonese
2011/0208031 A1 8/2011 Wolfe et al.
2011/0264038 A1 * 10/2011 Fujimoto ........ A61M 25/09041 604/95.01
2012/0041515 A1 2/2012 Meskens et al.
2012/0041531 A1 * 2/2012 Dadd ................... A61N 1/0541 607/116
2012/0071890 A1 3/2012 Taylor et al.
2012/0150293 A1 6/2012 Hoffman et al.
2012/0191107 A1 7/2012 Tanner et al.
2013/0138117 A1 5/2013 Abbott et al.
2013/0172901 A1 7/2013 Bozorg et al.
2013/0245569 A1 * 9/2013 Jolly ..................... A61M 31/00 604/272
2013/0296884 A1 11/2013 Taylor et al.
2013/0331779 A1 * 12/2013 Dhanasingh ........ A61M 31/002 604/93.01
2014/0135799 A1 * 5/2014 Henderson ........... A61B 17/221 606/138
2014/0200432 A1 7/2014 Banerji et al.
2014/0222207 A1 * 8/2014 Bowling ................ A61B 17/16 700/261
2014/0276391 A1 * 9/2014 Yu ........................ A61B 1/0016 604/95.01
2014/0276948 A1 9/2014 Zirps
2014/0277441 A1 9/2014 Reif et al.
2014/0350640 A1 * 11/2014 Patrick ................. A61N 1/0541 607/57
2014/0358174 A1 * 12/2014 Thenuwara .......... A61N 1/0551 606/190
2015/0032123 A1 1/2015 Jolly et al.
2015/0032124 A1 * 1/2015 Lenarz ............... A61B 17/3468 606/129
2015/0105795 A1 * 4/2015 Lenarz ................. A61N 1/0541 607/137
2015/0342445 A1 * 12/2015 Jones ................. A61B 1/00133 600/106
2016/0038733 A1 2/2016 Robinson et al.
2016/0045747 A1 2/2016 Jiang et al.
2016/0056493 A1 2/2016 Umeda et al.
2016/0243367 A1 8/2016 Li et al.
2017/0014998 A1 1/2017 Langenfeld et al.
2018/0021568 A1 * 1/2018 Schächtele ......... A61N 1/36038 607/137
2018/0064532 A1 3/2018 Ho et al.
2018/0242967 A1 * 8/2018 Meade ............... A61B 17/0469
2019/0029668 A1 * 1/2019 Meade ............... A61B 17/0491
2019/0142247 A1 * 5/2019 Maeda ................... A61B 1/018 600/106
2019/0282803 A1 * 9/2019 Hansen .............. A61N 1/36038
2020/0038106 A1 * 2/2020 Pieper .................... A61B 34/30
2020/0046978 A1 2/2020 Kaufmann et al.
2020/0069386 A1 * 3/2020 Betsugi .............. A61B 1/00045
2020/0329950 A1 * 10/2020 Shear ................... A61B 1/0016
2020/0337725 A1 10/2020 Kaufmann et al.
2021/0077252 A1 3/2021 Hoffman et al.
2021/0093869 A1 4/2021 Kaufmann et al.

(56) References Cited

U.S. PATENT DOCUMENTS

| | | | | |
|---|---|---|---|---|
| 2021/0187294 | A1* | 6/2021 | Kaufmann | A61N 1/0541 |
| 2021/0187295 | A1 | 6/2021 | Kaufmann et al. | |
| 2021/0196318 | A1 | 7/2021 | Kaufmann et al. | |
| 2022/0118246 | A1 | 4/2022 | Hansen et al. | |
| 2024/0293672 | A1 | 9/2024 | Kaufmann et al. | |
| 2025/0009388 | A1 | 1/2025 | Kaufmann et al. | |
| 2025/0235693 | A1 | 7/2025 | Kaufmann et al. | |
| 2025/0339687 | A1 | 11/2025 | Kaufmann et al. | |

FOREIGN PATENT DOCUMENTS

| | | | |
|---|---|---|---|
| CA | 2997735 | A1 | 3/2017 |
| CN | 101460219 | A | 6/2009 |
| CN | 104958108 | A | 10/2015 |
| CN | 107708616 | A | 2/2018 |
| CN | 110430918 | A | 11/2019 |
| CN | 112074254 | A | 12/2020 |
| CN | 114010372 | A | 2/2022 |
| CN | 115038398 | A | 9/2022 |
| CN | 116712667 | | 9/2023 |
| EP | 0634941 | B1 | 7/1997 |
| EP | 2113283 | A1 | 11/2009 |
| EP | 2615992 | B1 | 7/2016 |
| EP | 1906858 | B1 | 11/2016 |
| EP | 3334492 | A1 | 6/2018 |
| EP | 3334492 | B1 | 6/2019 |
| EP | 3662971 | A1 | 6/2020 |
| EP | 3582849 | | 8/2023 |
| EP | 3939544 | | 6/2025 |
| WO | WO-2010113072 | A2 | 10/2010 |
| WO | WO-2014145327 | A1 | 9/2014 |
| WO | WO-2017048342 | A1 | 3/2017 |
| WO | WO-2017177208 | A1 | 10/2017 |
| WO | WO-2018152203 | A2 | 8/2018 |
| WO | WO-2018152203 | A3 | 10/2018 |
| WO | WO-2019173107 | A1 | 9/2019 |
| WO | 2021038416 | | 3/2021 |
| WO | WO-2021067463 | A1 | 4/2021 |
| WO | WO-2023245167 | A2 | 12/2023 |
| WO | WO-2023245167 | A3 | 2/2024 |

OTHER PUBLICATIONS

"U.S. Appl. No. 15/759,643, Corrected Notice of Allowability mailed Dec. 30, 2021", 2 pgs.
"U.S. Appl. No. 15/759,643, Final Office Action mailed Mar. 29, 2021", 13 pgs.
"U.S. Appl. No. 15/759,643, Non Final Office Action mailed Sep. 4, 2020", 15 pgs.
"U.S. Appl. No. 15/759,643, Notice of Allowance mailed Sep. 28, 2021", 10 pgs.
"U.S. Appl. No. 15/759,643, Preliminary Amendment filed Mar. 13, 2018", 12 pgs.
"U.S. Appl. No. 15/759,643, Response filed Jun. 1, 2021 to Final Office Action mailed Mar. 29, 2021", 9 pgs.
"U.S. Appl. No. 15/759,643, Response filed Dec. 4, 2020 to Non Final Office Action mailed Sep. 4, 2020", 9 pgs.
"U.S. Appl. No. 16/486,030, Corrected Notice of Allowability mailed Jan. 12, 2021", 7 pgs.
"U.S. Appl. No. 16/486,030, Non Final Office Action mailed Sep. 8, 2020", 12 pgs.
"U.S. Appl. No. 16/486,030, Notice of Allowance mailed Dec. 24, 2020", 11 pgs.
"U.S. Appl. No. 16/486,030, Preliminary Amendment Filed Aug. 14, 2019", 10 pgs.
"U.S. Appl. No. 16/486,030, Response filed Aug. 10, 2020 to Restriction Requirement mailed Jun. 11, 2020", 8 pgs.
"U.S. Appl. No. 16/486,030, Response filed Dec. 8, 2020 to Non Final Office Action mailed Sep. 8, 2020", 12 pgs.
"U.S. Appl. No. 16/486,030, Restriction Requirement mailed Jun. 11, 2020", 7 pgs.
"U.S. Appl. No. 16/486,030, Supplemental Preliminary Amendment filed", 8 pgs.
"U.S. Appl. No. 16/926,335, Notice of Allowance mailed Nov. 9, 2020", 14 pgs.
"U.S. Appl. No. 16/926,335, Response filed Oct. 2, 2020 to Restriction Requirement mailed Aug. 4, 2020", 9 pgs.
"U.S. Appl. No. 16/926,335, Restriction Requirement mailed Aug. 4, 2020", 6 pgs.
"U.S. Appl. No. 16/979,427 Preliminary Amendment filed Sep. 9, 2020", 10 pgs.
"U.S. Appl. No. 17/038,916, Non Final Office Action mailed Apr. 27, 2023", 7 pgs.
"U.S. Appl. No. 17/038,916, Response filed Mar. 20, 2023 to Restriction Requirement mailed Jan. 20, 2023", 7 pgs.
"U.S. Appl. No. 17/038,916, Restriction Requirement mailed Jan. 20, 2023", 7 pgs.
"U.S. Appl. No. 17/180,087, Preliminary Amendment filed Apr. 12, 2021", 7 pgs.
"U.S. Appl. No. 17/196,690, Final Office Action mailed Jul. 10, 2023", 13 pgs.
"U.S. Appl. No. 17/196,690, Non Final Office Action mailed Dec. 22, 2022", 18 pgs.
"U.S. Appl. No. 17/196,690, Response filed Mar. 22, 2023 to Non Final Office Action mailed Dec. 22, 2022", 10 pgs.
"U.S. Appl. No. 17/196,723, 312 Amendment filed Sep. 21, 2021", 2 pgs.
"U.S. Appl. No. 17/196,723, Corrected Notice of Allowability mailed Jul. 7, 2021", 2 pgs.
"U.S. Appl. No. 17/196,723, Notice of Allowance mailed Jun. 23, 2021", 8 pgs.
"U.S. Appl. No. 17/196,723, PTO Response to Rule 312 Communication mailed Sep. 28, 2021", 2 pgs.
"U.S. Appl. No. 17/561,260, Non Final Office Action mailed Mar. 30, 2023", 16 pgs.
"U.S. Appl. No. 17/561,260, Preliminary Amendment filed Feb. 28, 2022", 7 pgs.
"Australian Application Serial No. 2016323477, First Examination Report mailed Jun. 29, 2020", 3 pgs.
"Australian Application Serial No. 2016323477, Response filed Dec. 10, 2020 to First Examination Report mailed Jun. 29, 2020", 19 pgs.
"Australian Application Serial No. 2019231573, First Examination Report mailed Feb. 8, 2021", 6 pgs.
"Australian Application Serial No. 2019231573, Response filed Apr. 27, 2021 to First Examination Report mailed Feb. 8, 2021", 40 pgs.
"Australian Application Serial No. 2019231573, Response filed Sep. 4, 2021 to Subsequent Examiners Report mailed May 11, 2021", 26 pgs.
"Australian Application Serial No. 2019231573, Subsequent Examiners Report mailed May 11, 2021", 3 pgs.
"Australian Application Serial No. 2020357745, First Examination Report mailed Mar. 16, 2023", 4 pgs.
"Australian Application Serial No. 2021232688, First Examination Report mailed Apr. 1, 2022", 4 pgs.
"Australian Application Serial No. 2021232688, Response filed Jul. 12, 2022 to First Examination Report mailed Apr. 1, 2022", 115 pgs.
"Canadian Application Serial No. 2997735, Office Action mailed Jun. 17, 2021", 4 pgs.
"Canadian Application Serial No. 2997735, Response filed Sep. 20, 2021 to Office Action Mailed Jun. 17, 2021", 62 pgs.
"Chinese Application Serial No. 201980030326.X, Office Action mailed Feb. 11, 2023", w/ English Translation, 23 pgs.
"Chinese Application Serial No. 201880011446.0, Office Action mailed Sep. 28, 2022", w/English Translation, 16 pgs.
"Chinese Application Serial No. 201880011446.0, Response filed Jan. 17, 2023 to Office Action mailed Sep. 28, 2022", w/ English claims, 12 pgs.
"Chinese Application Serial No. 201880011446.0, Voluntary Amendment filed Feb. 28, 2020", w/ English claims, 7 pgs.
"Chinese Application Serial No. 201980030326.X, Response filed Jun. 9, 2023 to Office Action mailed Feb. 11, 2023", w/ English Claims, 12 pgs.

(56) References Cited

OTHER PUBLICATIONS

"Chinese Application Serial No. 201980030326.X, Voluntary Amendment filed Mar. 24, 2021", with English translation of claims, 13 pgs.
"Chinese Application Serial No. 201980038179.0, Response to Examiner Telephone Interview filed Aug. 25, 2022", w/ English claims, 46 pgs.
"Chinese Application Serial No. 202080076185.8, Notification to Make Rectification mailed May 24, 2022", with machine translation, 2 pgs.
"European Application Serial No. 16736687.1, Intention to Grant mailed Jan. 7, 2019", 48 pgs.
"European Application Serial No. 18707575.9, Communication under Rule 71(3) EPC mailed May 9, 2022", 72 pgs.
"European Application Serial No. 18707575.9, Communication under Rule 71(3) EPC mailed Oct. 27, 2022", 76 pgs.
"European Application Serial No. 18707575.9, Response to Communication Pursuant to Rules 161 and 162 filed Feb. 25, 2020", 23 pgs.
"European Application Serial No. 19173377.3, Extended European Search Report mailed Mar. 4, 2020", 4 pgs.
"European Application Serial No. 19173377.3, Response filed Oct. 25, 2020 to Extended European Search Report mailed Mar. 4, 2020", 22 pgs.
"European Application Serial No. 19710939.0, Response to Communication pursuant to Rules 161(1) and 162 EPC filed Apr. 15, 2021", 29 pgs.
"European Application Serial No. 21192166.3, Extended European Search Report mailed Dec. 16, 2021", 11 pgs.
"European Application Serial No. 21192166.3, Response filed Jul. 1, 2022 to Extended European Search Report mailed Dec. 16, 2021", 29 pgs.
"International Application Serial No. PCT/US2016/039342, International Preliminary Report on Patentability mailed Mar. 29, 2018", 9 pgs.
"International Application Serial No. PCT/US2016/039342, International Search Report mailed Oct. 6, 2016", 4 pgs.
"International Application Serial No. PCT/US2016/039342, Written Opinion mailed Oct. 6, 2016", 7 pgs.
"International Application Serial No. PCT/US2018/018182, International Preliminary Report on Patentability mailed Aug. 29, 2019", 14 pgs.
"International Application Serial No. PCT/US2018/018182, International Search Report mailed Sep. 10, 2018", 7 pgs.
"International Application Serial No. PCT/US2018/018182, Invitation to Pay Add'l Fees and Partial Search Report mailed May 23, 2018", 15 pgs.
"International Application Serial No. PCT/US2018/018182, Written Opinion mailed Sep. 10, 2018", 12 pgs.
"International Application Serial No. PCT/US2019/020130, International Preliminary Report on Patentability mailed Sep. 24, 2020", 7 pgs.
"International Application Serial No. PCT/US2019/020130, International Search Report mailed Jun. 12, 2019", 7 pgs.
"International Application Serial No. PCT/US2019/020130, Written Opinion mailed Sep. 12, 2019", 10 pgs.
"International Application Serial No. PCT/US2020/053579, International Preliminary Report on Patentability mailed Apr. 14, 2022", 10 pgs.
"International Application Serial No. PCT/US2020/053579, International Search Report mailed Jan. 18, 2021", 3 pgs.
"International Application Serial No. PCT/US2020/053579, Written Opinion mailed Jan. 18, 2021", 8 pgs.
Campbell, Luke, et al., "Intraoperative Real-time Cochlear Response Telemetry Predicts Hearing Preservation in Cochlear Implantation", Otology & Neurotology; vol. 37(4), (Apr. 2016), 10 pgs.
Dahm, MC, et al., "The postnatal growth of the temporal bone and its implications for cochlear implantation in children", Acta Otolaryngol Suppl. 505., (1993), 4-39.
Desrosiers, M, et al., "Precise vocal cord medialization using an adjustable laryngeal implant: a preliminary study", Otolaryngol Head Neck Sur, 109(6), (1993), 1014-1019.
Fasano, Alfonso, et al., "MDS SIC Blog: Recent Advances in Deep Brain Stimulation (DBS) Technology", International Parkinson and Movement Disorder Society, [Online]. Retrieved from the Internet: <URL: https://www.movementdisorders.org/MDS/Scientific-Issues-Committee-Blog/Recent-Advances-in-DBS-Technology.htm>, (Mar. 2018), 3 pgs.
Gantz, Bruce J., et al., "Hybrid 10 Clinical Trial", Audiol Neurotol 2009; 14(suppl 1):DOI: 10.1159/000206493, (2009), 7 pgs.
Greene, Nathaniel, et al., "Intracochlear pressure transients during cochlear implant electrode insertion", Otol Neurotol. 37(10), (2016), 1541-1548.
Jurawitz, Marie-Charlot, et al., "Hearing Preservation Outcomes with Different Cochlear Implant Electrodes: Nucleus ® Hybrid™-L24 and Nucleus Freedom™ CI422", Audiol Neurotol 2014; 19: 293-309; DOI: 10.1159/000360601, (2014), 17 pgs.
Mittmann, Phillipp, et al., "Intracochlear Pressure Changes due to 2 Electrode Types: An Artificial Model Experiment", Otolaryngology—Head and Neck Surgery, vol. 156(4), (Dec. 2016), 712-716.
Montgomery, William, et al., "Montgomery Thyroplasty Implant for vocal fold immobility: phonatory outcomes", Ann Otol Rhinol Laryngol, 109(4), (2000), 393-400.
Mowry, Sarah E., et al., "New Frontiers in Cochlear Implantation: Acoustic Plus Electric Hearing, Hearing Preservation, and More", Otolaryngologic Clinics of North America. Volume 45, Issue 1., (2012), 187-203.
Woodson, Erika A., et al., "The Hybrid Cochlear Implant: A Review", Cochlear Implants and Hearing Preservation. Adv Otorhinolaryngol. Basel, Karger, 2010, vol. 67., (2010), 125-134.
"U.S. Appl. No. 17/196,690, Response filed Sep. 11, 2023 to Final Office Action mailed Jul. 10, 2023", 8 pgs.
"U.S. Appl. No. 17/196,690, Non Final Office Action mailed Sep. 28, 2023", 12 pgs.
"Chinese Application Serial No. 201980030326.X, Office Action mailed Sep. 20, 2023", with English Translation, 21 pgs.
"International Application Serial No. PCT US2023 068582, Invitation to Pay Additional Fees mailed Oct. 31, 2023", 5 pgs.
"U.S. Appl. No. 16/979,427, Non Final Office Action mailed Oct. 31, 2023", 14 pgs.
"European Application Serial No. 23190893.0, Extended European Search Report mailed Oct. 31, 2023", 6 pgs.
"U.S. Appl. No. 17/180,087, Notice of Allowance mailed Mar. 14, 2024", 14 pgs.
"U.S. Appl. No. 17/196,690, Corrected Notice of Allowability mailed Feb. 28, 2024", 2 pgs.
"U.S. Appl. No. 17/196,690, Notice of Allowance mailed Feb. 12, 2024", 8 pgs.
"U.S. Appl. No. 17/196,690, Response filed Dec. 20, 2023 to Non Final Office Action mailed Sep. 28, 2023", 7 pgs.
"Chinese Application Serial No. 201980030326.X, Response filed Nov. 20, 2023 to Office Action mailed Sep. 20, 2023", w/ English claims, 12 pgs.
"International Application Serial No. PCT/US2023/068582, International Search Report mailed Dec. 21, 2023", 4 pgs.
"International Application Serial No. PCT/US2023/068582, Written Opinion mailed Dec. 21, 2023", 10 pgs.
"U.S. Appl. No. 17/180,087, Corrected Notice of Allowability mailed Jun. 25, 2024", 2 pgs.
"U.S. Appl. No. 18/661,059, Non Final Office Action mailed Aug. 29, 2024", 13 pgs.
"U.S. Appl. No. 18/743,727, Preliminary Amendment filed Sep. 30, 2024", 6 pgs.
"U.S. Appl. No. 18/661,059, Examiner Interview Summary mailed Nov. 21, 2024", 2 pgs.
"U.S. Appl. No. 18/661,059, Response filed Nov. 27, 2024 to Non Final Office Action mailed Aug. 29, 2024", 9 pgs.
"International Application Serial No. PCT US2023 068582, International Preliminary Report on Patentability mailed Dec. 26, 2024", 11 pgs.
"U.S. Appl. No. 18/661,059, Notice of Allowance mailed Jan. 15, 2025", 9 pgs.

(56) References Cited

OTHER PUBLICATIONS

"Chinese Application Serial No. 202111075017.X, Office Action mailed Jan. 18, 2025", W English Translation, 18 pgs.
"U.S. Appl. No. 18/661,059, Corrected Notice of Allowability mailed May 1, 2025", 4 pgs.
"U.S. Appl. No. 19/183,505, Preliminary Amendment filed Jul. 28, 2025", 5 pgs.
"European Application Serial No. 23190893.0, Communication Pursuant to Article 943 EPC mailed Sep. 18, 2025", 4 pgs.
"U.S. Appl. No. 18/743,727, Notice of Allowance mailed Oct. 28, 2025", 8 pgs.
"U.S. Appl. No. 19/462,833, Preliminary Amendment filed Feb. 17, 2026", 3 pgs.
"Chinese Application Serial No. 202310560680.1, Office Action mailed Apr. 17, 2026", w English Translation, 11 pgs.

* cited by examiner

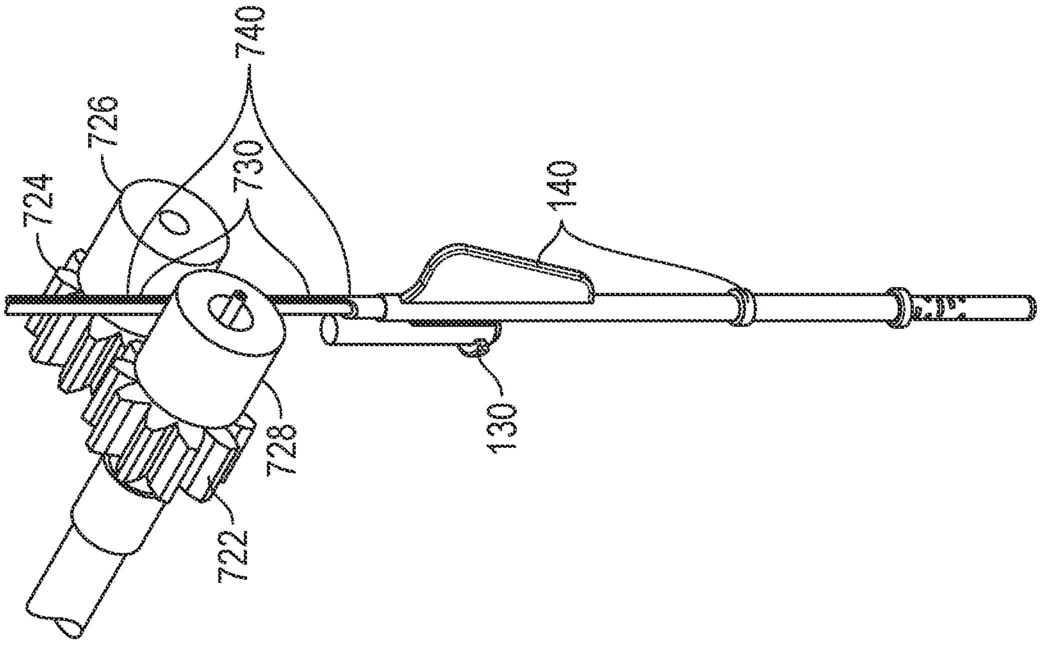
FIG. 3E
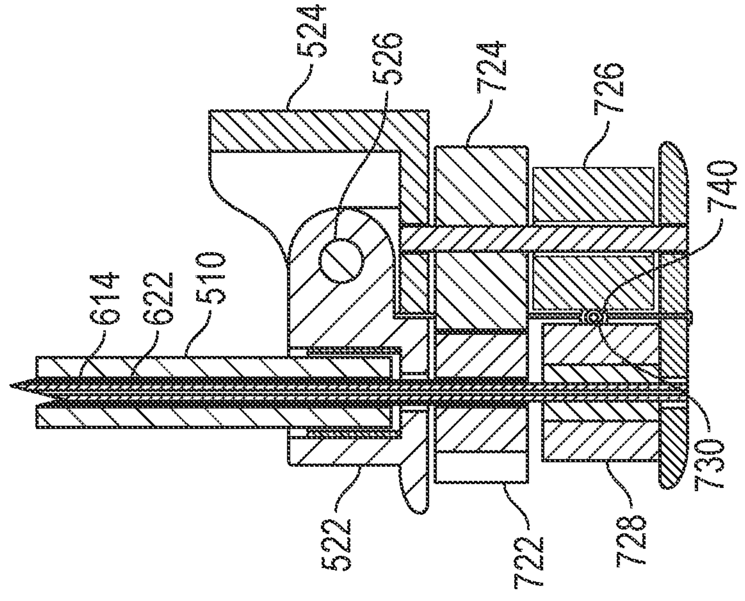
FIG. 3D
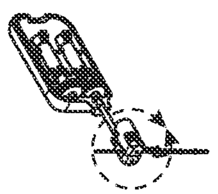

SYSTEMS AND METHODS FOR MANIPULATION OF PERIMODIOLAR ELECTRODE ARRAYS

CLAIM OF PRIORITY

This patent application is a continuation in part of U.S. patent application Ser. No. 17/180,087, filed Feb. 19, 2021, which application is a continuation of U.S. patent application Ser. No. 16/926,335, filed Jul. 10, 2020, which application is a continuation in part of PCT Application No. PCT/US2019/020130, filed Feb. 28, 2019, which application claims the benefit of priority to U.S. Provisional Patent Application No. 62/640,964, filed Mar. 9, 2018. U.S. patent application Ser. No. 16/926,335 is also a continuation in part of U.S. patent application Ser. No. 16/486,030, filed Aug. 14, 2019, which application is a U.S. National Stage Filing under 35 U.S.C. 371 from International Application No. PCT/US2018/018182, filed on Feb. 14, 2018, which application claims the benefit of priority to U.S. Provisional Patent Application No. 62/458,846, filed Feb. 14, 2017, and U.S. Provisional Patent Application No. 62/573,487, filed Oct. 17, 2017. U.S. patent application Ser. No. 16/926,335 also claims the benefit of priority to U.S. Provisional Patent Application No. 62/872,625, filed Jul. 10, 2019. This patent application also claims the benefit of priority to U.S. Provisional Patent Application No. 63/353,364, filed Jun. 17, 2022. Each of which are incorporated by reference herein in their entireties.

STATEMENT REGARDING FEDERALLY SPONSORED RESEARCH OR DEVELOPMENT

This invention was made with government support under award number R44DC017640 awarded by the Department of Health and Human Services. The government has certain rights in this invention.

TECHNICAL FIELD

This document relates generally to medical systems and more particularly to systems, devices, and methods for robotic control of delivery, positioning, and manipulation of a perimodiolar electrode array.

BACKGROUND

The cochlea is the auditory portion of the inner ear. It comprises a spiraled, hollow, conical chamber of bone in which sound waves propagate from the base to the apex of the cochlea. The sound waves vibrate the perilymph that moves hair cells in the organ of *Corti*, converting the vibrations to electrical signals that are sent to the cochlear nerve. The hair cells and nerves in the basal or outer region of the spiraled cochlea are more sensitive to higher frequencies of sound and are frequently the first part of the cochlea to lose sensitivity. The apical or inner region of the spiraled cochlea is more sensitive to lower frequencies.

Moderate to profound hearing loss affects a large amount of people worldwide and may have a significant impact on a patient physical and mental health, education, employment, and overall quality of life. Hearing loss may be caused by partial damage to the cochlea. Many patients with various degrees of hearing loss have partial damage to the cochlea in the high-frequency regions (basal cochlea) from common causes such as noise exposure, drugs, genetic mutations, or aging, but may retain adequate low-frequency hearing.

Cochlear implants have been used to treat patients with hearing loss. A cochlear implant is a medical device that comprises an external sound processor, a subcutaneously implantable stimulator, and an electrode assembly sized and shaped for cochlear insertion. The sound processor can convert sound signals into electrical signals and transmit the electrical signals to the implantable stimulator. Based on the physical properties (e.g., frequencies) of the received electrical signals, the stimulator can generate electrical impulses to stimulate specific regions in the cochlea via an array of electrodes on the electrode assembly surgically inserted into the cochlea. The region for stimulation may be determined based on the frequencies of the received electrical signals. For example, higher frequencies may result in stimulation at the outer or basal cochlear region, and lower frequencies may result in stimulation at the inner or apical cochlear region.

For patients who have lost high-frequency hearing and consequently have significant difficulty with word understanding but who have substantial residual, low-frequency hearing function in apical cochlea, a short electrode assembly may be indicated to electrically stimulate the basal or outer cochlea to restore high-frequency hearing. A cochlear implant surgery may be performed by a surgeon to manually insert the electrode assembly into the damaged portion of a patient cochlea (e.g., basal cochlea), while avoiding or minimizing any trauma to the undamaged cochlear regions to preserve the low-frequency hearing function. The cochlear implant may be used together with a hearing aid that acoustically stimulates the undamaged low-frequency sensitive apical cochlea.

The electrode placement in cochlear implant surgery is a crucial step that plays a significant role in the success of the procedure. The following outlines a few key aspects of electrode placement, such as insertion technique, insertion depth, number of electrodes, preservation of residual hearing, intraoperative testing, and imaging and surgical guidance. The surgeon carefully inserts the electrode array into the cochlea, which is the part of the inner ear responsible for converting sound into electrical signals that can be transmitted to the brain. The array is designed to be gently threaded through the cochlea to ensure that the electrodes come into close contact with the auditory nerve fibers. The depth to which the electrode array is inserted into the cochlea is an essential consideration. The surgeon aims to achieve a balance between maximizing the coverage of the cochlea and avoiding damage to delicate structures. The exact insertion depth depends on factors such as the individual's anatomy, the size and shape of their cochlea, and the surgeon's expertise. Cochlear implant electrode arrays consist of multiple electrodes that are designed to stimulate different regions of the cochlea. The number of electrodes can vary depending on the specific device being used. The goal is to place a sufficient number of electrodes to cover the frequency range of speech and other important sounds. In some cases, individuals undergoing cochlear implant surgery may have some residual hearing in low-frequency regions of the cochlea. Whenever possible, the surgeon may try to preserve this residual hearing by avoiding damage to those areas during electrode insertion. This can be achieved through techniques such as electrode arrays with thin, flexible designs or by using specialized surgical approaches. During the surgery, intraoperative testing is often performed to assess the neural responses to electrical stimulation. These tests help the surgical team determine the optimal placement and functioning of the electrode array. Intraoperative testing may involve measures such as impedance testing, electrically evoked auditory brainstem response (EABR), or neural response telemetry (NRT). In recent years, advances in imaging techniques and surgical navigation technology have improved the accuracy of electrode placement. Preoperative imaging, such as high-resolution computed tomography (CT) scans or magnetic resonance imaging (MRI), can provide detailed information about the patient's cochlear anatomy. Surgical navigation systems may assist the surgeon in precisely positioning the electrode array based on this preoperative imaging. Ultimately, the goal of electrode placement in cochlear implant surgery is to achieve optimal contact between the electrodes and the auditory nerve fibers, ensuring effective electrical stimulation and subsequent transmission of sound signals to the brain. The expertise and experience of the surgical team, along with technological advancements, contribute to improving the accuracy and outcomes of electrode placement.

As noted above, one potential complication during electrode insertion is intracochlear trauma. Intracochlear trauma can occur from large pressure spikes generated during the insertion of cochlear implant electrodes. Cochlear implant surgery can also involve insertion of a guide sheath or tube near or partially into the cochlea. Insertion of any solid or flexible bodies, tubes, or sheaths into the cochlea could elicit similar fluid and force spikes. These pressures spikes may be of sufficient intensity to cause trauma similar to that of an acoustic blast injury and are one likely source for postoperative loss of residual hearing. Similar to the insertion trauma cause by electrode insertion, the manual insertion of a sheath or other solid body/tube manually into the cochlea may cause intracochlear fluid pressure spikes and result in intrachochlear damage.

SUMMARY

A hearing-preservation cochlear implant surgery involves implanting an electrode assembly into the damaged cochlear region, while avoiding any trauma to the undamaged cochlear region to preserve any normal residual hearing. In current cochlear implant surgery, a surgeon manually inserts an electrode assembly into patient cochlea. However, a complete manual maneuvering of the electrode assembly may cause undesirable outcome in some patients. For example, manual insertion of electrode assembly may lack precision in implant position and motion control, such as the control of insertion rate, distance, or forces applied to the implant for advancing the electrode assembly to the target cochlear region. This may cause damage to fragile cochlear structures such as local trauma to cochlea wall and hair cells and result in residual hearing loss.

Complete manual maneuvering of the electrode assembly may also be subject to high inter-operator variability among surgeons. The inter-operator variability is demonstrated in dramatic differences in patient outcomes between institutions and surgeons of differing skill levels. Some patients undergoing hearing-preservation cochlear implant surgery may experience additional hearing decline weeks to years after surgery. Such a continual decline in hearing function may be attributed to an inflammatory response to the trauma inflicted during an initial cochlear implant surgery. Some clinical studies show that techniques aimed at reducing electrode-insertion forces during surgery have improved patient hearing preservation outcomes. For at least reasons, the present inventors have recognized that there remains a need to improve patient outcome following a hearing-preservation cochlear implant surgery, particularly systems, apparatus, and methods that enhance surgical precision in implant delivery and positioning as well as reducing the risk of perioperative trauma to undamaged cochlea region.

This document discusses, among other things, systems, devices, and methods for robotically assisted implantation of an implant in a patient, such as for delivering and positioning a cochlear implant for treating hearing loss in a hearing-preservation cochlear implant surgery. The systems and devices discussed are specifically designed and adapted for robotically controlling insertion of a perimodiolar electrode array. The modular system discussed herein includes an external positioning unit reversibly interfacing with and securely engaging an implant such as a cochlear implant having an elongate member, and a computerized control unit for robotically controlling the external positioning unit to regulate the motion of the implant. The computerized control unit may have a user interface that enables a user (e.g., a surgeon) to program various motion control parameters or to select an implantation protocol. The system may include sensors providing feedback on the position or the motion of the implant, or the force or friction applied to the implant during the implantation procedure. The sensors can include navigation markers to enable optical or electromagnetic navigation of the electrode and/or sheath. The computerized control unit may regulate the motion of the implant based on user input and the sensor feedback. The control systems may also interface with external systems providing electrophysiological measurements to enable closed loop feedback on electrode positioning in real-time during implantation.

The systems, devices, and methods discussed in this document may improve the technological field of robotic surgery, particularly robotically assisted implantation of an implant or prosthesis. For example, when the systems or methods discussed herein are used in hearing-preservation cochlear implant surgery, the robotic motion control of the cochlear implant (specifically a perimodiolar electrode array) may reduce the mechanical forces imposed on the delicate cochlear structure such as basilar membrane and organ of *Corti*, thereby minimizing the risk of trauma on the undamaged structure such as at the apical cochlea. This may ultimately better preserve patient residual natural hearing. Compared to manual insertion and steering of a cochlear implant, the robotically assisted cochlear implantation may allow more people with disabling hearing loss to hear better over their lifetimes.

The external positioning unit is a non-implanted external device. Compared to a partially or completely implantable insertion device, the external positioning unit discussed herein may substantially reduce the risk of complications associated with surgical implantation, extraction, or replacement of otherwise partially or completely implantable insertion device. The external positioning unit also has the advantage of easy troubleshooting, maintenance, and replacement, thereby reducing cost of the system and the procedure. As to be discussed in the following, the external positioning unit may have a small size with limited mechanical and electrical parts, thus making it flexible for external fixation to a patient. The external position unit can be affixed to the patient, affixed to an adjacent piece of equipment, or be handheld, among other affixation options considered within the scope of this disclosure.

Although the discussion in this document focuses on a perimodiolar electrode array implant, this is meant only by way of example and not limitation. It is within the contemplation of the present inventors, and within the scope of this document, that the systems, devices, and methods discussed herein may be configured for robotically delivering, steering, positioning, or extracting various types of implants or prosthesis. By way of non-limiting examples, the implants may include leads, catheter, guidewire, or other mechanical or electrical devices. The implants may be designed for temporary or permanent implantation. The implants may be used for medical diagnosis of a disease or other conditions such as diagnostic catheters, or for therapeutic purposes of cure, mitigation, treatment, or prevention of disease, such as implantable electrodes for stimulating cardiac, neural, muscular, or other tissues. In addition to new implantation, the systems, devices, and methods discussed herein may also be used to surgically reposition or replace an existing implant.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 3A-3E illustrate, by way of example and not limitation, different views of another embodiment of an implant-positioning unit for engaging and manipulating a perimodiolar electrode array.

DETAILED DESCRIPTION

Figure 1A:
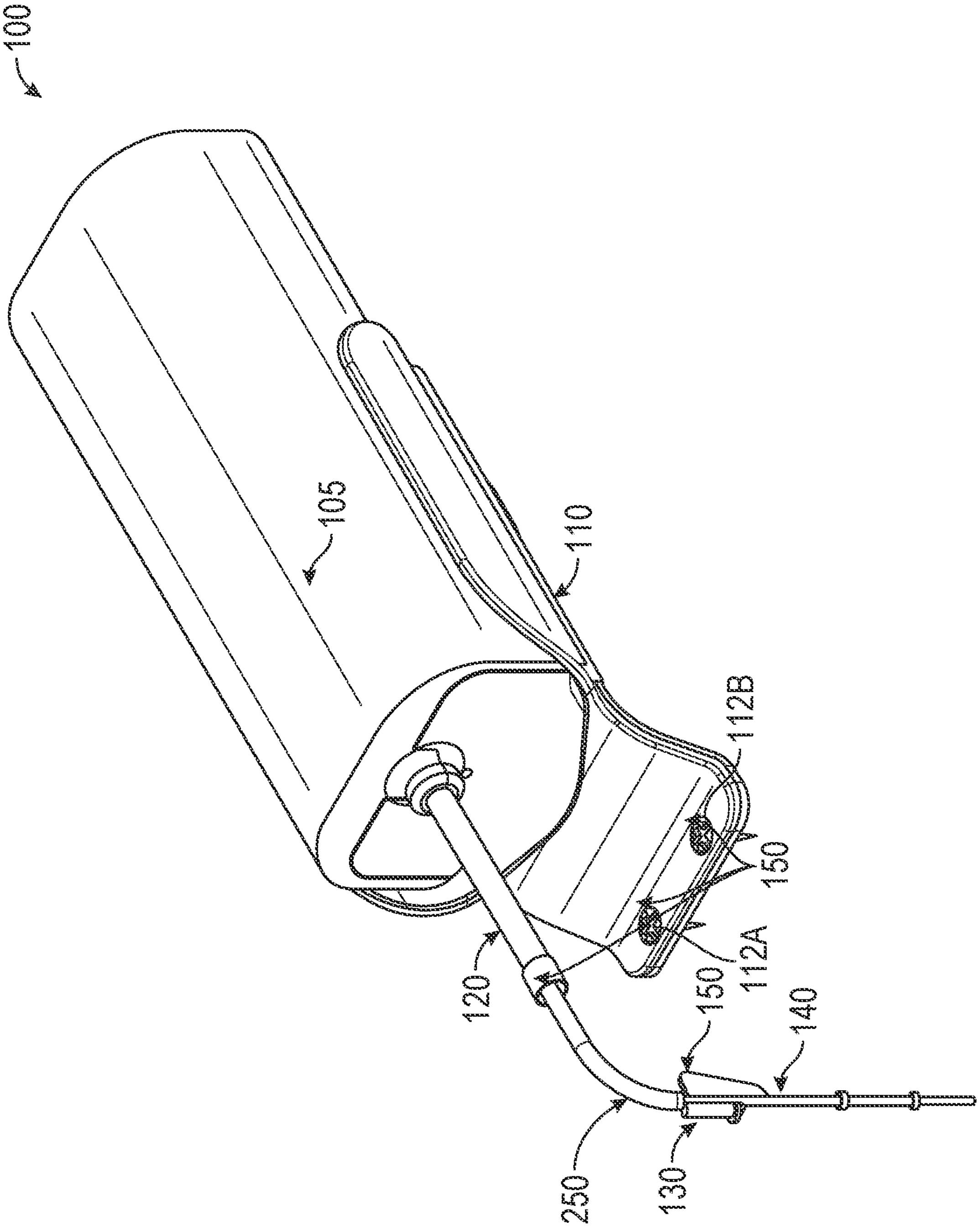
FIGS. 1A-1E illustrate, by way of example and not limitation, a robotically assisted implantation system and portions of an environment in which the robotically assisted implantation system may operate for manipulation of a perimodiolar electrode array.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical, and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Disclosed herein are systems, devices, and methods for robotically assisted implantation of an implant in a patient. More specifically, disclosed are various embodiments of a robotically assisted device for implantation of a perimodiolar electrode array. Examples of the implants may include leads, catheter, guidewire, guide sheath, or other mechanical or electrical devices. The implants may be designed for temporary or permanent implantation. The implants may additionally be used for medical diagnosis of a disease or other conditions such as diagnostic catheters, or for therapeutic purposes of cure, mitigation, treatment, or prevention of disease, such as implantable electrodes for stimulating cardiac, neural, muscular, or other tissues. As noted above, the present inventions are discussed in view of manipulation of a cochlear electrode and associated delivery sheath. The present system may be implemented using a combination of hardware and software designed to provide precise control of implant movement, such as insertion of a cochlear implant during a hearing-preservation cochlear implant surgery or positioning or manipulation of a cochlear implant in a thyroplasty surgery. The system includes an implant-positioning unit a control console communicatively coupled to the implant-positioning unit. The implant-positioning unit includes a drive head configured to engage an elongate member of the implant and robotically deliver and position the implant into a target implantation site. The control console may have a user interface that enables a user to input motion control instructions. The control console may generate a motion control signal, according to a specific motion control instruction, to control the external positioning unit to propel the implant into a target implant site.

The included figures depict various embodiments of a robotically assisted implantation system optimized for use with perimodiolar electrode arrays. The robotically assisted implantation system consists of an enclosure housing, two or more motor assemblies providing torque independent of one another, two or more lead screws rotated by each motor, and two or more carriages actuated linearly by turning of the screws. Another example includes two or more motors coupled to a co-axial drive cable to transmit rotational movement to a drive head with multiple drive wheels. Yet another example, can utilize linear actuators to, directly or in-directly, manipulate the electrode and sheath independently.

The robotically assisted implantation system also utilizes a flexible portion of the outside sheath positioning cable as well as a flexible portion of the inside electrode positioning cable. In an example, the positioning cable is a coaxial cable with the outside sheath positioning cable surrounding the inside electrode positioning cable to deliver either linear actuation to the electrode and/or sheath or torque from the motors to a drive head (see alternative embodiments discussed further below).

The housing includes an exit port for the positioning cables to travel concentrically out of the enclosure, through a flexible gooseneck tubing or adjustable semi-rigid arm, to the electrode/sheath assembly. More generally, the positioning cables or similar structures can extend out of a housing through an adjustable drive transmission conduit between the housing and a drive head. Gooseneck is used within the specification to describe an adjustable drive transmission conduit or similar structure.

The outside sheath positioning cable can include a flexible wound cable with a hollow lumen and rigid end, capable of transmitting rotation, pushing, and pulling through a flexible gooseneck or an adjustable semi-rigid arm. The outside sheath positioning cable can also be attached with a revolute joint on one end to a carriage and on the other end rigidly to the sheath. When linearly actuated by the carriage either forward or backward the outside sheath positioning cable can transmit linear movement advancing or retracting the sheath or other instrumentation independent of the other movement. In some examples, a third motor and gear may rotate the outside sheath positioning cable within the enclosure controlling the orientation of the sheath and therefore the orientation of the pre curved electrode insertion. In certain examples, a third motor and friction wheel assembly can be incorporated to enable rotational control over the electrode during insertion.

The inside electrode positioning cable can include a flexible wound cable with a rigid end, capable of transmitting rotation, pushing, and pulling through a flexible gooseneck or an adjustable semi-rigid arm and outside sheath positioning cable. The inside electrode positioning cable can be attached with a revolute joint on one end to a carriage and on the other end can push an electrode array or other instrumentation. When linearly actuated by the carriage either forward or backwards the inside electrode positioning cable can transmit linear movement advancing or retracting the electrode independent of the sheath movement.

The attachment between the outside sheath positioning cable and the sheath may be a friction-based press fit as depicted or may be an annular snap joint, or a cantilever snap joint, or graspers, or magnetic coupling. Alternatively, the sheath may be integrated into the rigid portion of the outside sheath positioning cable as once continuous piece eliminating the attachment to a 3rd party sheath.

The attachment between the inside electrode positioning cable and the electrode may be a friction-based press fit as depicted or may be an annular snap joint, or a cantilever snap joint, or graspers, or magnetic coupling.

The device is capable of advancing both the electrode and sheath together to or through the round window, into the cochlea, to the first turn. Then only the pre curved electrode is advanced forward out of the sheath around the turns of the cochlea while keeping the sheath stationary. And finally, the sheath is retracted while keeping the electrode stationary until the sheath and electrode disengage and the entire device is removed.

The device is securely mounted in a stage/base that is attached to the patient using bone screws, sutures, adhesives, or straps. In other examples, the stage/based of the system can be mounted or secured to a bed or any rigid structure within the adjacent surgical field. In still other examples, the stage/base is adapted to be handheld. The device (e.g., external positioning device) may be mounted directly to the stage base or to a gooseneck as an adjustable rigid arm that is connected or a part of the stage/base itself. The stage, device, and sheath may have fiduciary markers for 3D (three dimensional) position tracking feedback. The motors may have rotary encoders for position tracking feedback while the carriages may have linear encoders for position tracking feedback.

The motors used within the robotically assisted implantation system can be electro-magnetic motors, piezo-electric motors, or may be replaced with knobs/wheels turned manually by hand. In these examples, each motor may be controlled using one or more foot pedals, console controller, or other controller. Each motor may be integrated into a closed loop positioning feedback system using one or more of rotary encoders, linear encoders, pressure sensors, torque sensors, or physiological feedback. In yet further examples, the motors and additional mechanical mechanisms can be replaced with linear electric motors or linear actuators.

The semi-rigid support arm used within the robotically assisted implantation system can be made of segmented balls and cylinders with a tension cable running down the center lumen. In an example, to move the arm tension is released and when in position, tension is reapplied making the entire arm rigid. Tension control can be controlled through lever actuation, button actuation, wheel actuation, or motor actuation.

FIGS. 1A-1E illustrate a robotically assisted implantation system 100 for manipulation of a perimodiolar electrode array electrode 130. One of the key aspects of the system 100 is the ability to robotically manipulate both an electrode (such as electrode electrode 130) and an associated sheath sheath 140. The sheath sheath 140 is used to assist in implantation of the electrode electrode 130, such as by straightening a length of a naturally curved electrode, among other things. The systems discussed herein can also be utilized to manipulate other components such as sensing electrodes, stimulating electrodes, lights, lasers, cameras, or irrigation tools, among other things.

The system 100 can include components such as device enclosure 105, stage base 110, and gooseneck 120. The stage base 110 can include mounting screws 112 (mounting screw 112A and mounting screw 112B, collectively referenced as mounting screws 112) to assist in securing the stage base 110 to the patient temporary for the procedure. The gooseneck 120 provides a semi-rigid conduit for transmission of linear actuation from the drive assembly within the device enclosure 105. In certain examples, the gooseneck 120 is adjustable to accommodate different orientations between the device enclosure 105/stage base 110 and the patient. In other words, the gooseneck 120 is an example of an adjustable drive transmission conduit. The stage base 110 can be adapted for fixation via a clamp to a bed (or other equipment within the surgical field), a microscope, surgical instruments such as a retractor, or a bone or other part of the patient. The stage base 110 can also be adapted to be handheld during a procedure. In certain procedures, navigation system can be used to assist in determining and/or maintaining an optimal insertion trajectory of the electrode 130. In this example, the system 100 includes multiple fiducial markers 150 (in the drawings, the references 150 point to example locations for fiducial markers, the fiducial markers are not specifically illustrated) that can be used by a navigation system to coordinate determining and/or maintaining a trajectory for the electrode 130. The fiducial markers 150 could be optical or electromagnetic markers, among other well-known options for surgical navigation.

Figure 1B:
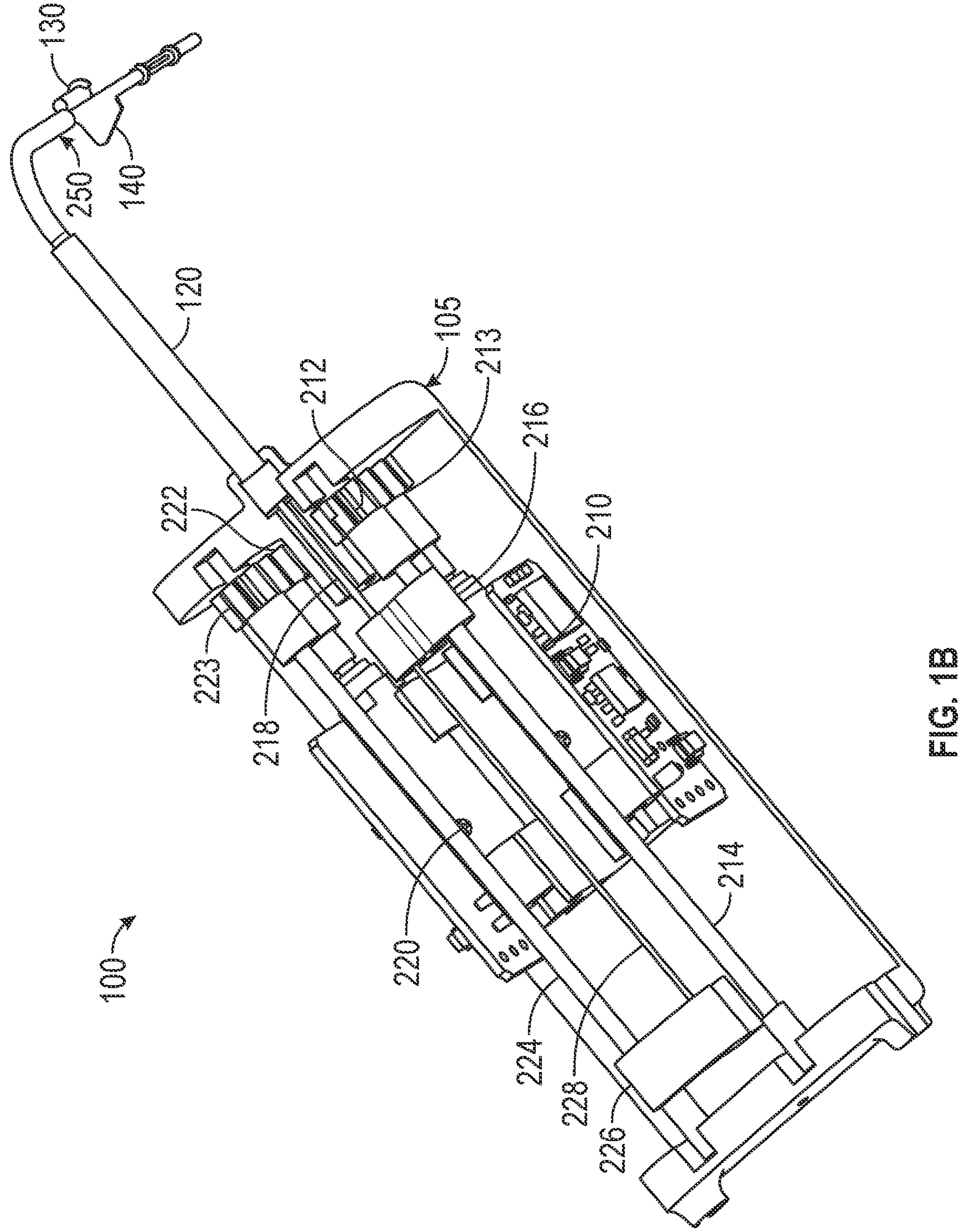
Figure 1C:
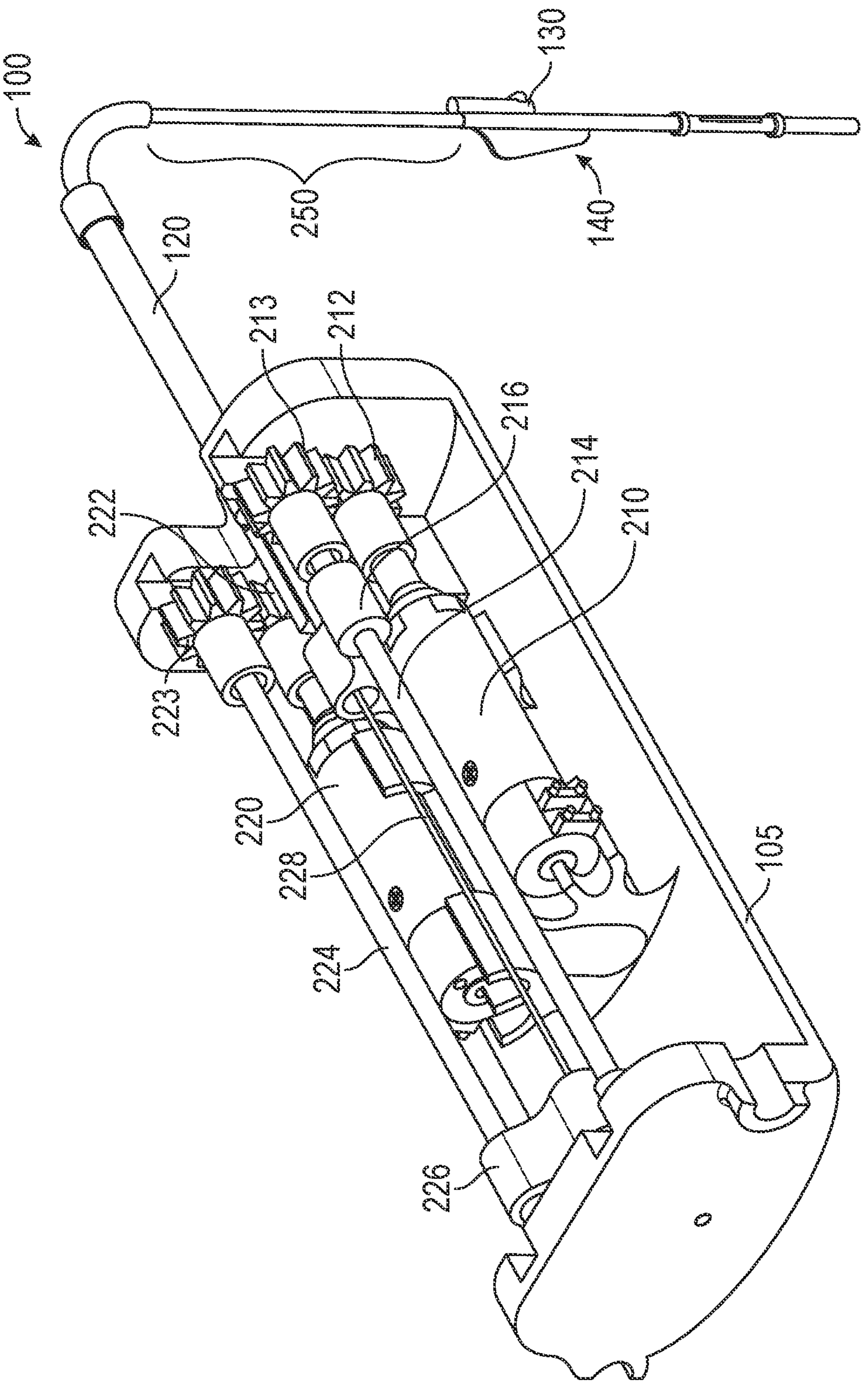

FIGS. 1B and 1C illustrate the inner workings of the system 100 in various views. As shown in these figures, in this example, the system 100 includes actuation components dedicated to either electrode actuation (movement) or sheath actuation. In general, the system 100 includes an electrode actuator and a sheath actuator, where each actuator includes components such as a motor, gears, a lead screw, a carriage, and control cables to deliver actuation through a flexible elongate body (gooseneck or adjustable drive transmission conduit) to a drive head. As noted above, the actuators discussed in this embodiment can be alternatively implemented with linear electric motors or linear actuators of various types. The sheath 140 is manipulated by a combination of a sheath motor 210 coupled to a sheath lead screw 214 through a sheath motor gear 212 and a sheath lead screw gear 213. Rotation of the sheath lead screw 214 moves a sheath carriage 216 which in turn moves a sheath position control cable 218 that runs through the gooseneck 120 to a drive head 250 where the sheath position control cable 218 couples to the sheath 140. Similarly, the electrode 130 is manipulated through a combination of an electrode motor 220 coupled to an electrode lead screw 224 through an electrode motor gear 222 and an electrode lead screw gear 223. Rotation of the electrode lead screw 224 moves an electrode carriage 226 which in turn manipulates an electrode positioning control cable 228 that runs through the gooseneck 120 into the drive head 250 and interacts with the electrode 130. In this example, the control cable is a coaxial cable that includes the electrode positioning control cable 228 running through the middle of the sheath position control cable 218. The term coaxial is utilized in describing the physical structure of the positioning control cable that, in this example, contains an outer cylindrical cable with an inner cable. In this example, the inner and outer cables can move independently or together.

In another example, a linear motor system can be substituted into system 100 for the motor, gears, lead screw, and carriage. In such an example, the sheath position control cable 214 and the electrode position control cable 228 are each connected to a linear motor, such as a linear electric motor or direct drive linear motor actuator. Linear actuation of the linear electric motor or linear actuator is transmitted to drive head 250 via the position control cables (as discussed herein).

Figures 1D, 1E:
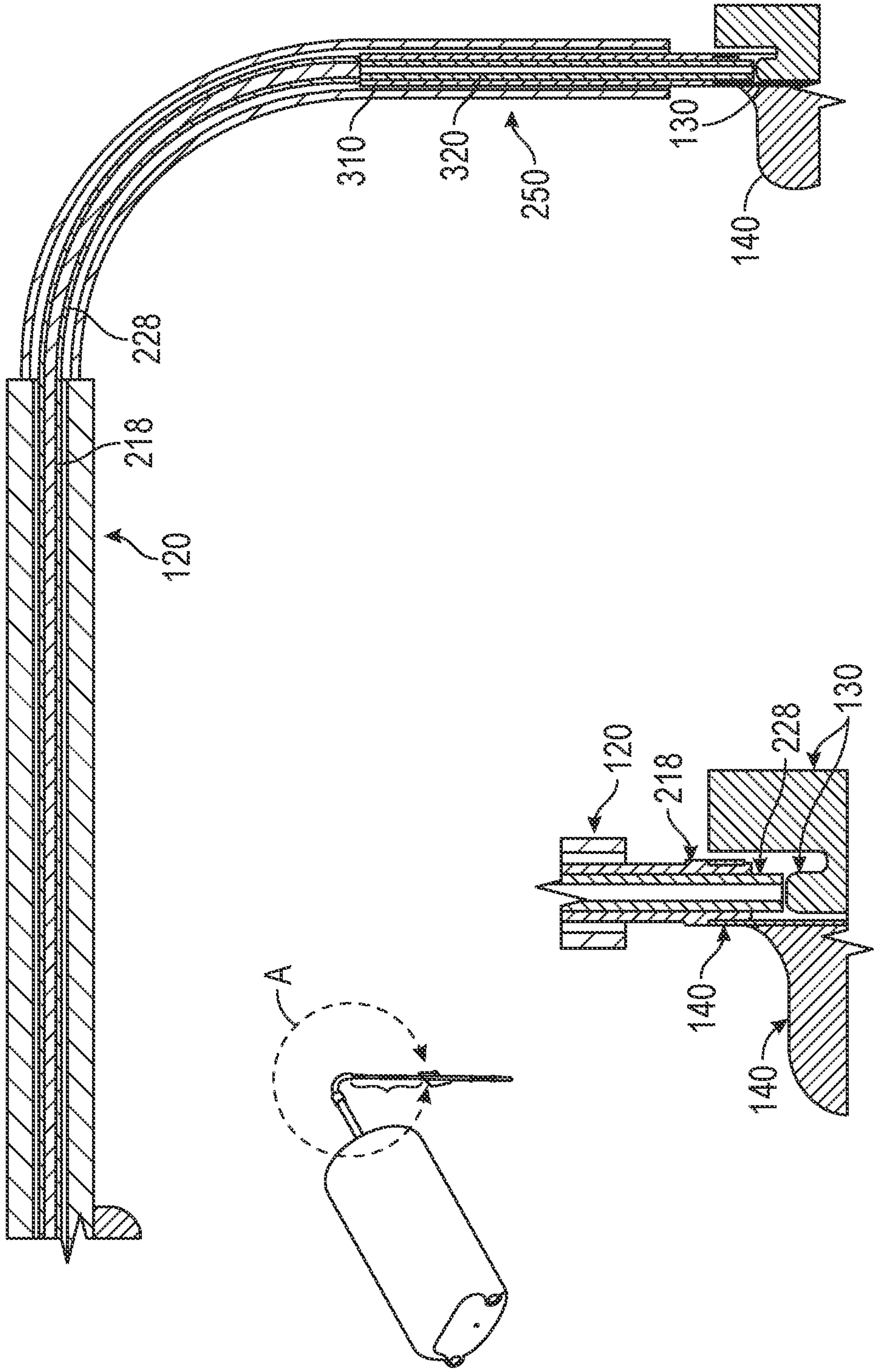

FIG. 1D is a cross-sectional view of a portion of system 100 that includes the gooseneck 120, the drive head 250, and parts of the electrode 130 and sheath 140. In this example, the control cables (sheath position control cable 218 and electrode positioning control cable 228) couple to positioning tubes that in turn engage the electrode 130 and the sheath 140. In this example, the drive head 250 includes a sheath positioning tube 310 and an electrode positioning tube 320. The sheath positioning tube 310 is coupled to a distal end of the sheath position control cable 218. The sheath position control cable 218 couples to a proximal end of the sheath positioning tube 310 and a distal end of the sheath positioning tube 310 press-fit (or similarly coupled) to a proximal end of the sheath 140 (see detail in FIG. 1E). Similarly, a distal end of the electrode positioning control cable 228 is coupled to a proximal end of an electrode positioning tube 320, which extends through the sheath positioning tube 310 and couples at a distal end to a proximal end of the electrode 130. In this example, the distal end of the electrode positioning tube 320 merely engages (e.g., pushes) the proximal end of the electrode 130. Other connections between the electrode positioning tube 320 and the electrode 130 are within the scope of this disclosure.

Figure 2B:
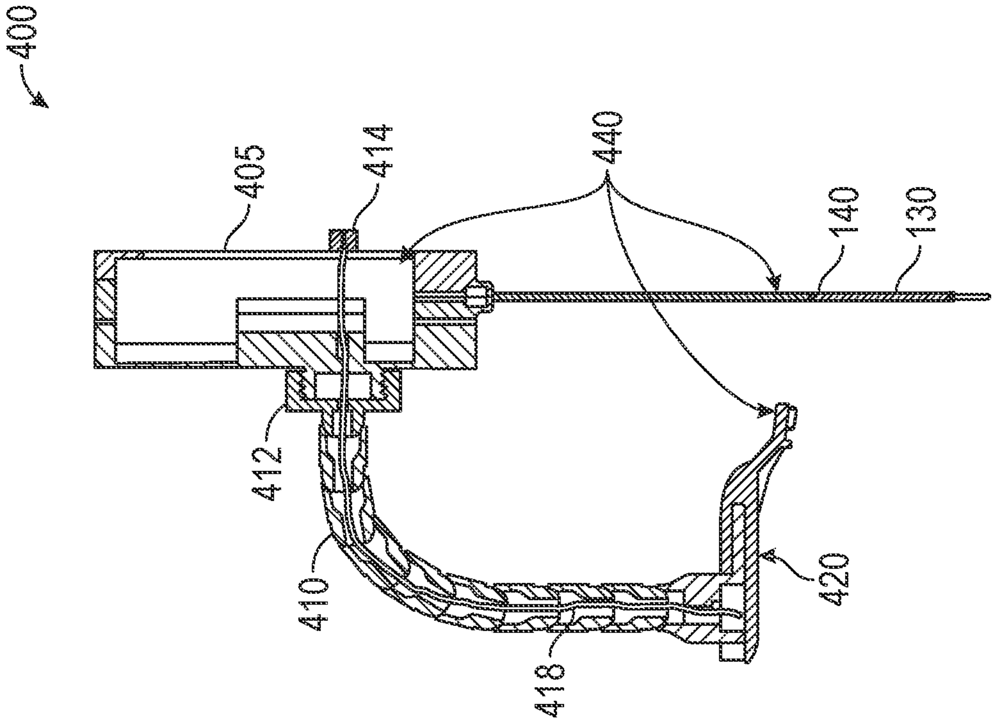
FIGS. 2A-2B illustrate, by way of example and not limitation, different views of another embodiment of an implant positioning unit including a mounting base and adjustable arm.
Figure 2A:
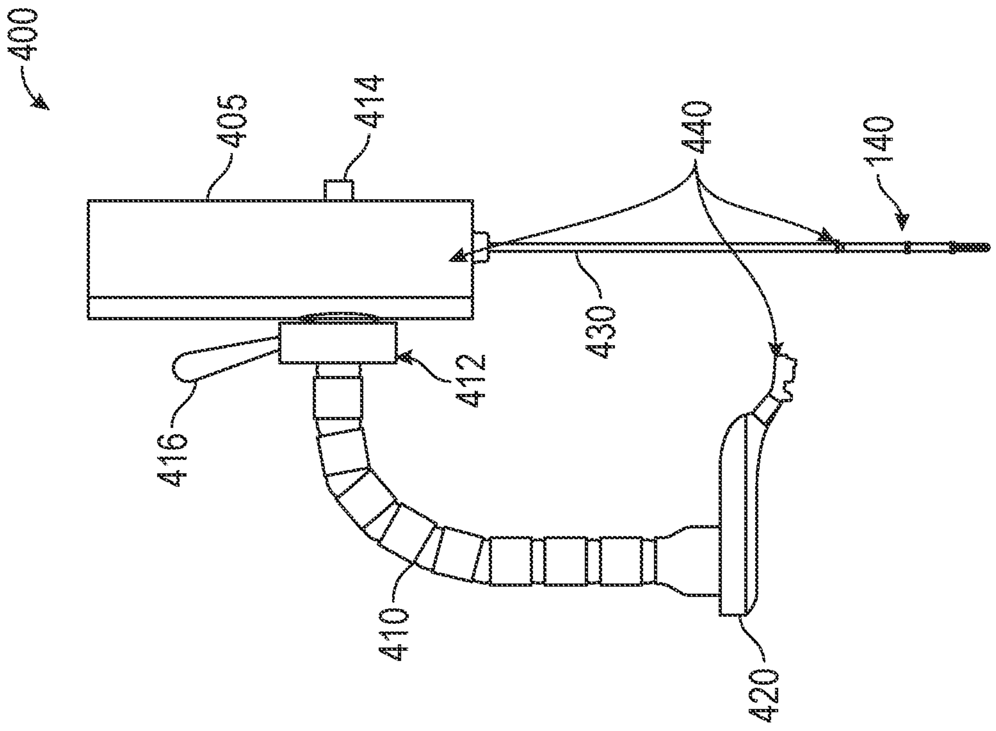

FIGS. 2A-2B illustrate an implant positioning system 400 including a mounting base and adjustable arm. In this example, the system 400 can include an enclosure 405 held in position by an adjustable arm 410 that is connected to a stage base 420. The stage base 420 is adapted for securing the system to the patient or adjacent equipment within the surgical field, as well as to being handheld during insertion operations. The adjustable arm 410 includes a locking mechanism that allows for the adjustable arm 410 to be freely adjustable to hold the enclosure 405 in a desire position and locked into the adjusted position. In this example, the locking mechanism can include a tension cable 418 manipulated by one or more of a tension wheel 412, a tension button 414, and/or a tension lever 416. The tension cable 418 within the adjustable arm 410 can be adjusted (e.g., tension) via the tension wheel 412 and/or tension button 414. In an example, the tension on the tension cable 418 can be applied or disengaged via the tension lever 416 (which can be coupled to the tension wheel 412 or be a separate adjustment mechanism). Tension on the tension cable 418 forces the segments of the adjustable arm 410 to lock into position relative to one another, which creates a rigid arm to hold the enclosure 405.

The system 400 can also include other features, such as a rigid actuator 430 and fiducial markers 440. The rigid actuator 430 can be a rigid tube that transmits actuation components, such as those discussed above, to manipulate the electrode 130 and the sheath 140. While the fiducial markers 440 are included to allow for the use of surgical navigation systems in conjunction with this embodiment.

FIGS. 3A-3E illustrate different views of another embodiment of an implant-positioning unit for engaging and manipulating a perimodiolar electrode array. The implant-positioning unit in this example can include an enclosure housing having two or more motor assemblies, two or more gears, and an exit port. The two or more motor assemblies can provide torque independent of one another. The two or more gears can transmit torque from the 2nd motor to an outside torque cable. The exit port includes an outside torque cable and the inside torque cable to travel concentric out of the enclosure through a flexible gooseneck arm or semi-rigid adjustable arm and attach to drive gears within the drive head.

The drive head allows rotation from the inside torque cable to pass through the drive head gear and turn the first drive wheel (associated with the electrode or electrode actuator). The outside torque cable rotation is transferred to the left side of the drive head through two spur gears and rotates the second drive wheel associated with the sheath (or sheath actuator).

The outside sheath actuator can be a rigid half tube down the length of itself with one end a whole tube capable of attaching rigidly to a sheath. The inside electrode actuator sits within the outside sheath actuator and is exposed on one half.

The first drive wheel can turn and frictionally engage the inside electrode actuator advancing or retracting it independently. The second drive wheel can turn and frictionally engage the outside sheath actuator advancing or retracting it independently.

In this example, the attachment between the Outside Sheath Actuator and the Sheath may be a press fit as depicted or may be an annular snap joint or a cantilever snap joint. In another example, not depicted in any figure does not attach to a 3rd party sheath but rather the Outside Sheath Actuator and the Sheath are one continuous piece, eliminating the need for a connection between the two.

In the illustrated example, the device is capable of advancing both the electrode and sheath together through the round window, into the cochlea, to the first turn. Then only the pre curved electrode is advanced forward out of the sheath around the turns of the cochlea while keeping the sheath stationary. And finally, the sheath is retracted while keeping the electrode stationary until the sheath and electrode disengage and the entire device is removed.

Figure 3B:
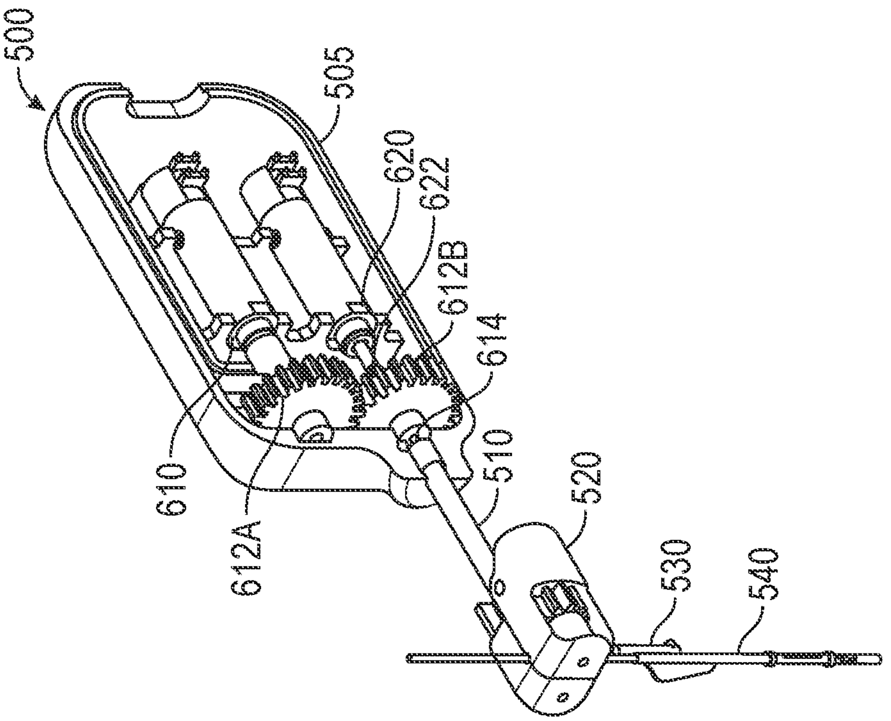
Figure 3A:
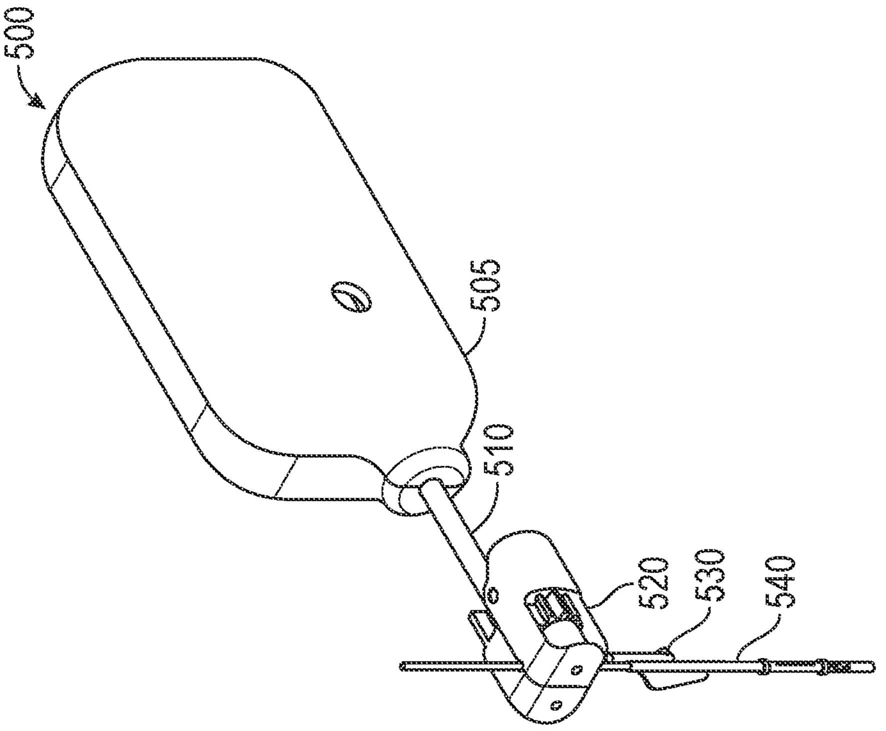

In an example, the FIGS. 3A-3E illustrate an implant positioning system 500. The system 500 can include components such as an enclosure 505, a gooseneck 510, and a drive head 520 that operate to manipulate an electrode 530 and a sheath 540. FIG. 3B is a cut-away view to illustrate some of the internal components of the system 500, such as a sheath motor 610 and an electrode motor 620. In this example, the torque/rotation generated by the sheath motor 610 is transmitted to the drive head 520 via sheath gears 612 (sheath gear 612A and sheath gear 612B, collectively referred to as the sheath gears 612) and a sheath torque cable 614. The torque/rotation generated by the electrode motor 620 is transmitted to the drive head 520 via an electrode torque cable 622. In this example, the electrode torque cable 622 runs inside the sheath torque cable 614, which together form a coaxial torque cable transmitting torque and/or rotation to the drive head 520.

Figure 3C:
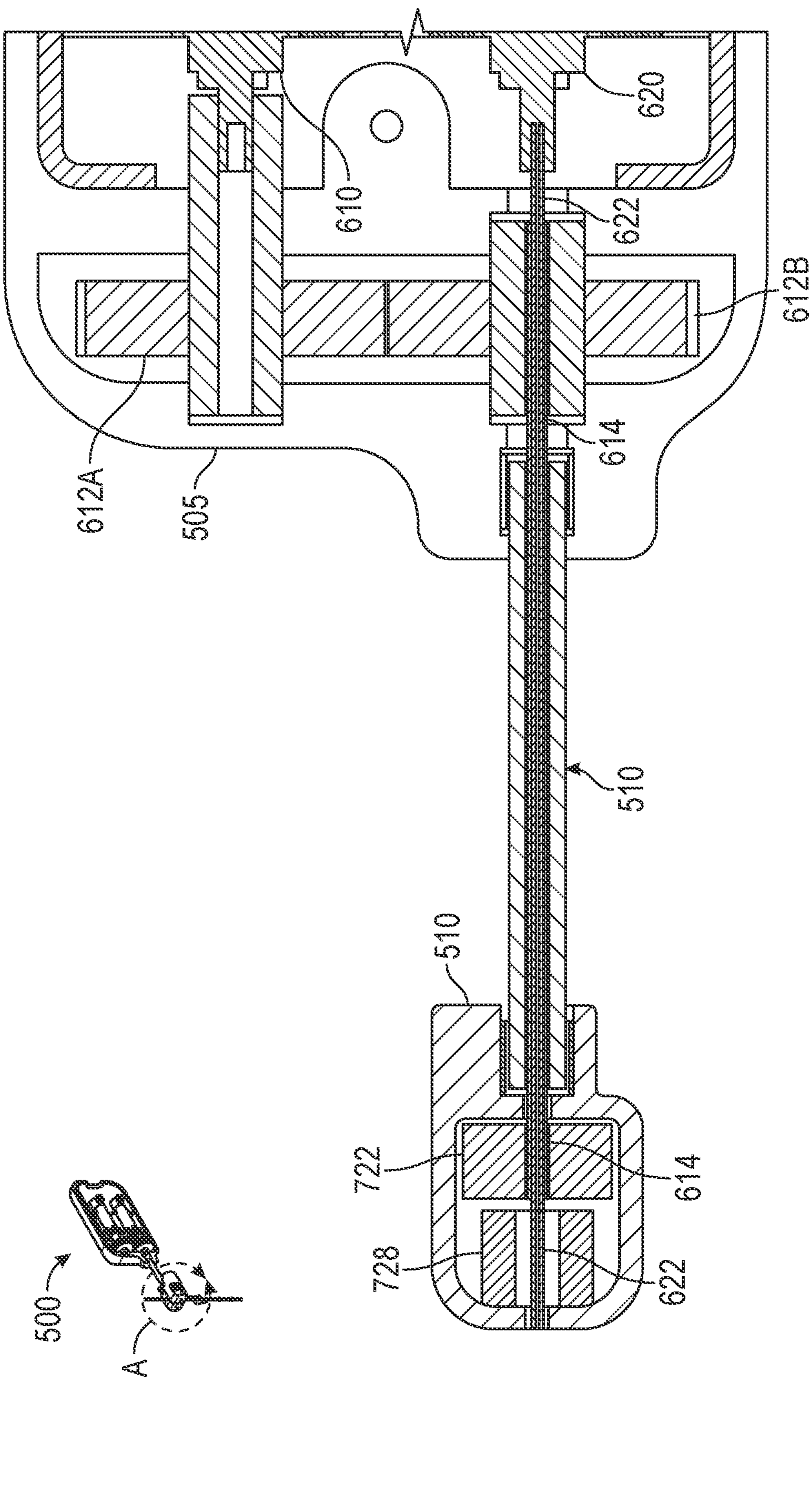

FIG. 3C is a cross-sectional view of the torque/rotation transmission mechanism within the enclosure 505 and the drive head 520. In this example, it is easier to visualize the relationship between the sheath torque cable 614 and the electrode torque cable 622. The combined torque cable (e.g., sheath torque cable 614 and electrode torque cable 622) run through the gooseneck 510 to the drive head 520. Within the drive head 520, the electrode torque cable 622 is coupled to an electrode drive wheel 728 that will ultimately drive an electrode actuator 730 to manipulate the electrode 530 (not shown in this figure). The sheath torque cable 614 is coupled to a sheath drive head gear one 722 that operates with another gear to transmit torque/rotation to a sheath drive wheel 726 (see FIG. 3D).

FIGS. 3D and 3E are various views of the components within the drive head 520 in this example. The illustrated drive head 520 can include a right drive head enclosure 522 and a left drive head enclosure 524 coupled together by a drive head hinge 526 that allows the two sides to pivot open for easy access. The drive mechanism within the drive head 520 can include the sheath drive head gear one 722 and the sheath drive head gear two 724 that transmit torque/rotation to the sheath drive wheel 726 which manipulates the sheath actuator 740. The drive mechanism also includes the electrode drive wheel 728 that is driven by the electrode torque cable 622 to manipulate the electrode actuator 730. As illustrated in FIG. 3E, the sheath actuator 740 includes a cut away portion on the proximal end that exposes the electrode actuator 730 to allow manipulation by the electrode drive wheel 728. The half cylinder proximal portion of the sheath actuator 740 interfaces with the sheath drive wheel 726 to allow for manipulation of the sheath actuator 740 (which in turn allows manipulation of the sheath 140). Similarly, the electrode actuator 730 is coupled to the electrode 130 and movement of the electrode actuator 730 translates into movement of the electrode 130. The length of the cut-away proximal portion of the sheath actuator 740 dictates the total range of motion of the electrode 130 and the sheath 140 with the system 500.

FIGS. 4A-4D are diagrams illustrating by way of example different views of a sheath embodiment for manipulation of a perimodiolar electrode array. FIGS. 4A-4D depict a sheath embodiment that can straighten a normally curved electrode as well as allow for quick removal of the sheath. Two split halves revolve around an open center axis holding an electrode. When opened the sheath halves rotate changing the completely enclosed tube into an opened half tube.

A perimodiolar pre-curved electrode array may be placed into the opened sheath. Once the sheath is closed the electrode array may be retracted into the straight sheath. Once retracted the sheath acts as a straight introducer to the round window of the cochlea and the electrode may be pushed through the top of the closed sheath in order to perform the electrode insertion into the cochlea. Once completely inserted the sheath may be opened and removed leaving only the inserted pre curved electrode array in place.

Figure 4B:
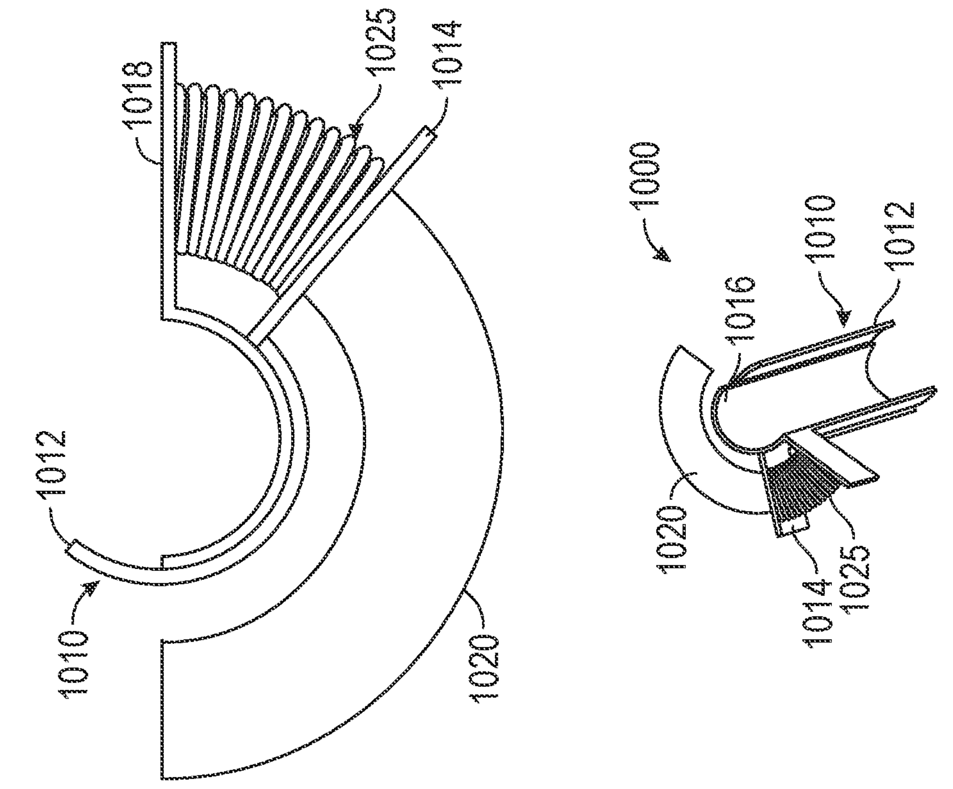
FIGS. 4A-4D are diagrams illustrating, by way of example and not limitation, different views of a sheath embodiment for manipulation of a perimodiolar electrode array.
Figure 4A:
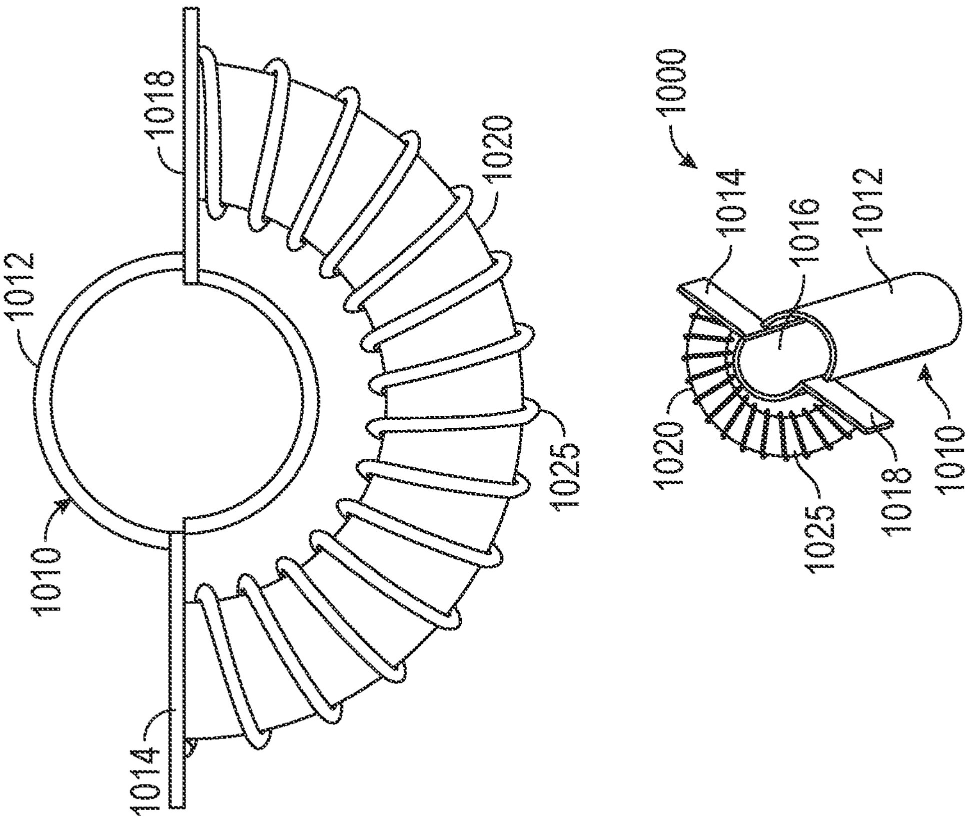
Figure 4C:
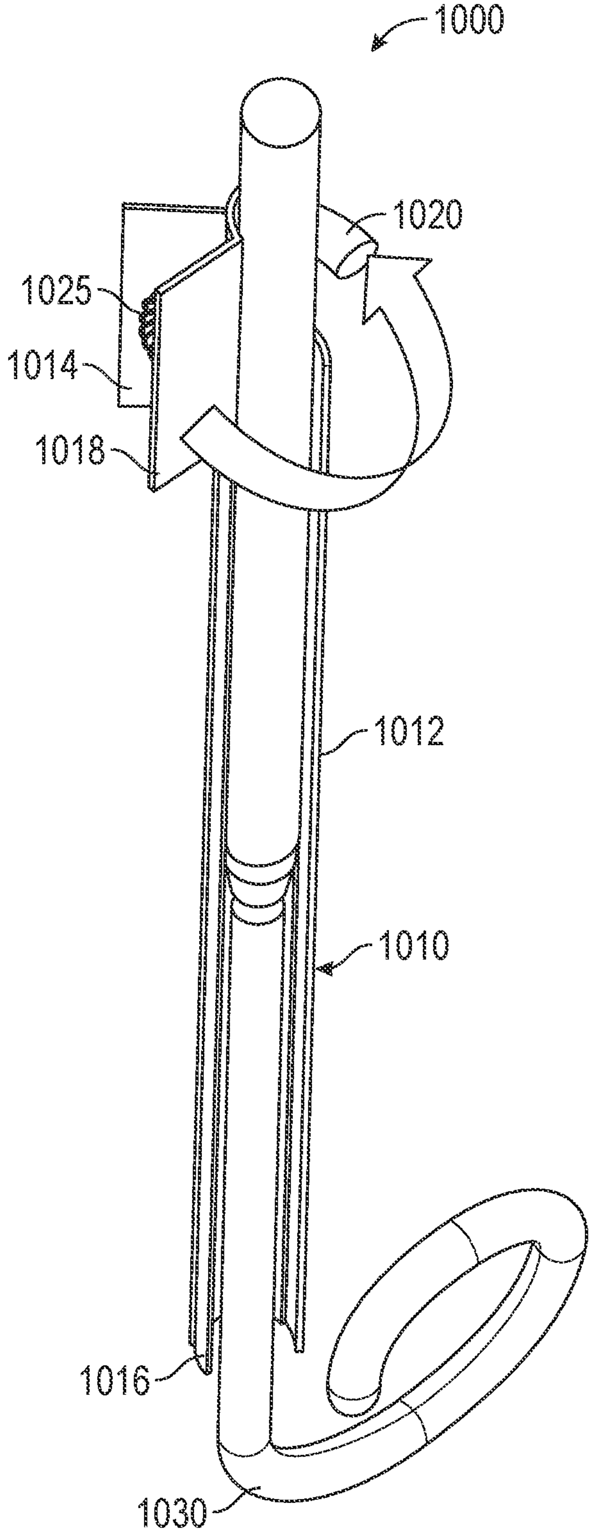
Figure 4D:
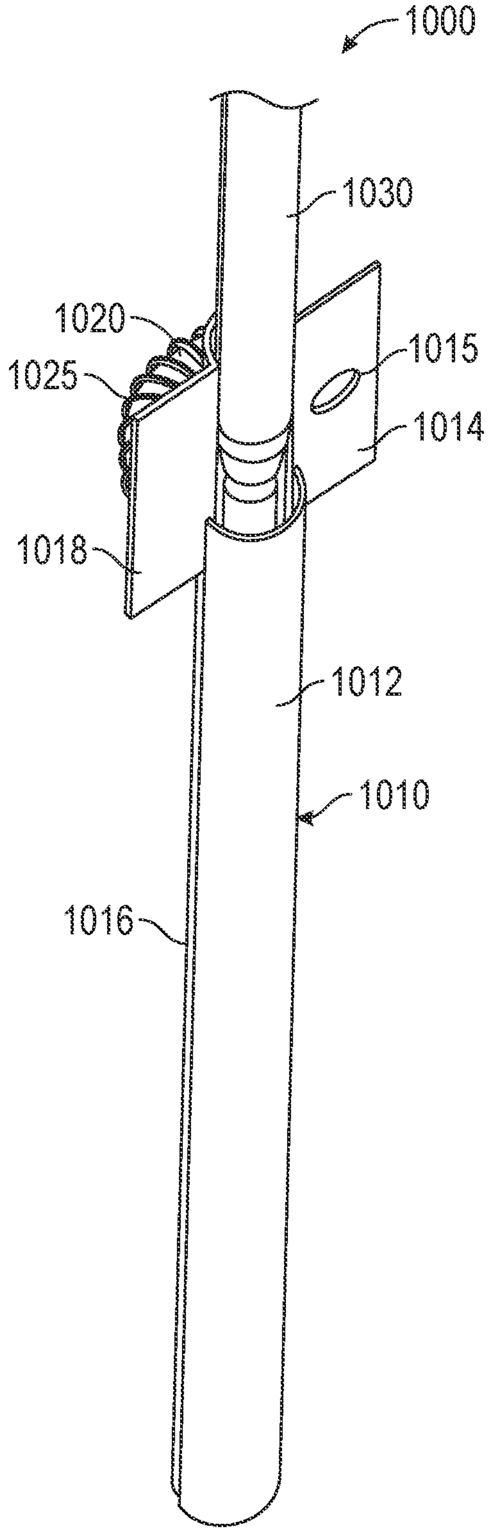

In this example, the rigid opening sheath 1000 illustrated in FIGS. 4A-4D can include structures such as a sheath 1010, a spring mandrel 1020, and spring 1025. The sheath 1010 can include a outside half sheath 1012 and a inside half sheath 1016 that rotate around a longitudinal axis running through the rigid opening sheath 1000 from a proximal end to a distal end. The outside half sheath 1012 can include a outside tab 1014 that includes a through bore to receive the spring mandrel 1020 upon rotation of the outside half sheath 1012 into an open position (as depicted in FIG. 4B). The inside half sheath 1016 includes a inside tab 1018 from which the spring mandrel 1020 extends in a semi-circular arc around a portion of the outside of the rigid opening sheath 1000. The spring mandrel 1020 includes a spring 1025 that extends from the outside tab 1014 to the inside tab 1018 along the length of the spring 1025 with the device in the closed position. In this example, the spring 1025 operates to bias the device into a closed position (e.g., the state illustrated in FIG. 4A). FIGS. 4C and 4D illustrate the full length of the rigid opening sheath 1000 in an open (FIG. 4C) and closed (FIG. 4D) positions with the electrode 1030 in position within the rigid opening sheath 1000. In FIG. 4C, the electrode 1030 is inserted into the open rigid opening sheath 1000, and in FIG. 4D the electrode 1030 is pulled back into the closed rigid opening sheath 1000 to straighten the electrode 1030 for insertion.

FIGS. 5A-5H are multiple views illustrating a manipulation section positioning assembly 1200 of a robotically assisted implantation system to manipulate a perimodiolar electrode array. In this example, a manipulation section or mechanism (as referred to as a positioning assembly 1200) can be used within a system, such as system 500 discussed in reference to FIGS. 3A-3E above. In this example, the positioning assembly 1200 includes an electrode drive assembly 1230 to control an electrode 1210 and a sheath drive assembly 1240 to control a sheath 1220. The electrode drive assembly 1230 includes two basic components an electrode pinion 1234 and an electrode elongated rack 1236, while the sheath drive assembly 1240 includes three four components a sheath drive gear one 1232, a sheath drive gear two 1242, a sheath drive pinion 1244, and a sheath elongated rack 1246. In this example, the gears, sheath drive gear one 1232 and sheath drive gear two 1242, correspond to gears, sheath drive head gear one 722 and sheath drive head gear two 724 in system 500. The primary difference between the positioning assembly 1200 and a comparable positioning assembly within system 500 is the use of the electrode elongated rack 1236 and sheath elongated rack 1246 engaged by the respective pinion (e.g., electrode pinion 1234 and sheath drive pinion 1244). The electrode elongated rack 1236 includes a distal end coupled to (or interfacing with) a proximal end of the electrode 1210 with movement of the electrode elongated rack 1236 translating directly into movement of the electrode 1210. Similarly, the sheath elongated rack 1246 includes a distal end coupled to a proximal end of the sheath 1220 and movement of the sheath elongated rack 1246 translates directly into movement of the sheath 1220. Movement of the electrode elongated rack 1236 and the sheath elongated rack 1246 occurs through a rack and pinion interaction between the grooves in each of the electrode elongated rack 1236 and the sheath elongated rack 1246 and protrusions in the radial surface of the electrode pinion 1234 and the sheath drive pinion 1244 respectively.

Figure 5A:
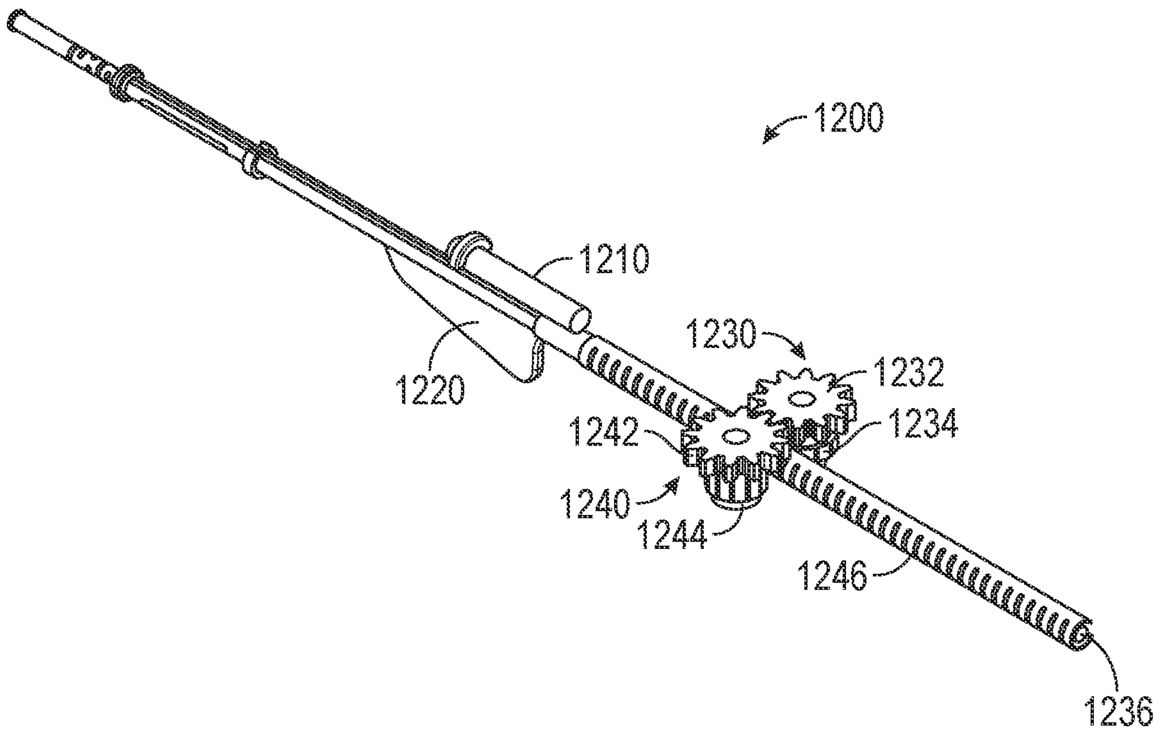
FIGS. 5A-5H are multiple views illustrating, by way of example and not limitation, the functioning of yet another embodiment of a portion of a robotically assisted implantation system designed to manipulate a perimodiolar electrode array.
Figure 5B:
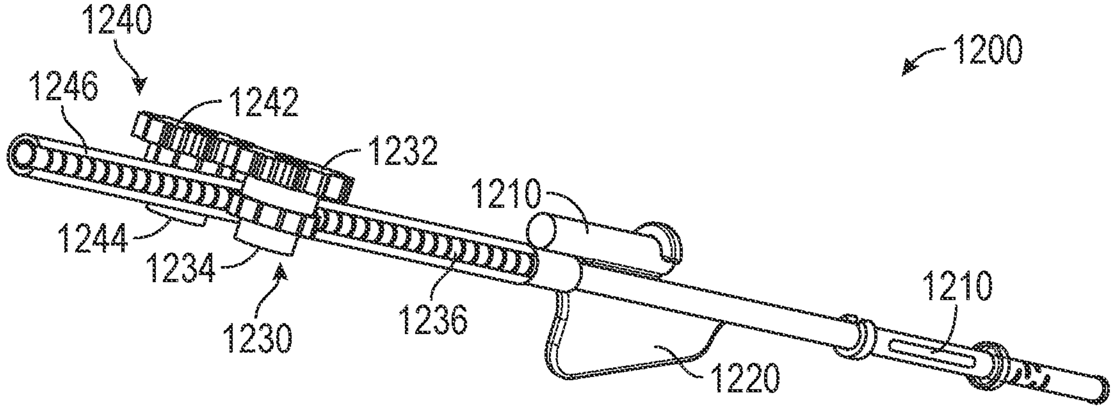
Figure 5C:
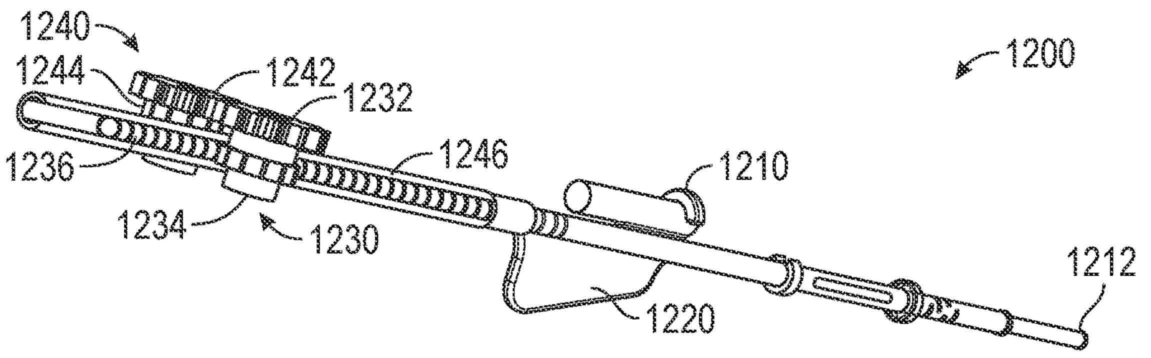
Figure 5D:
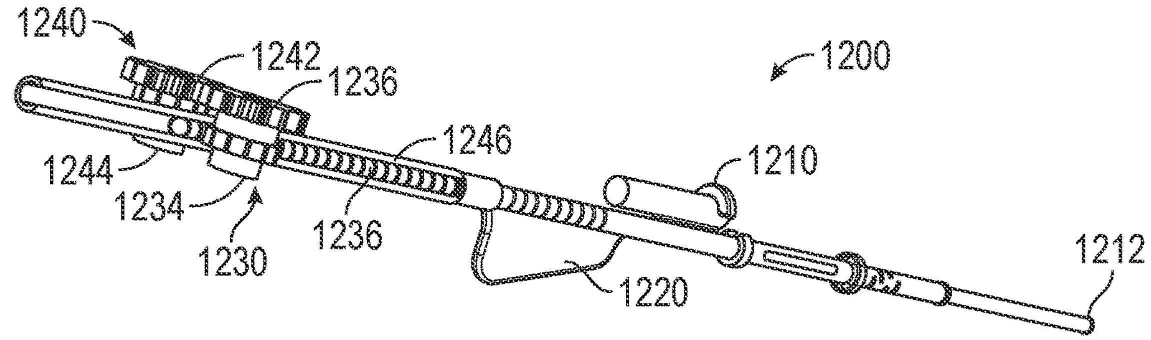
Figure 5E:
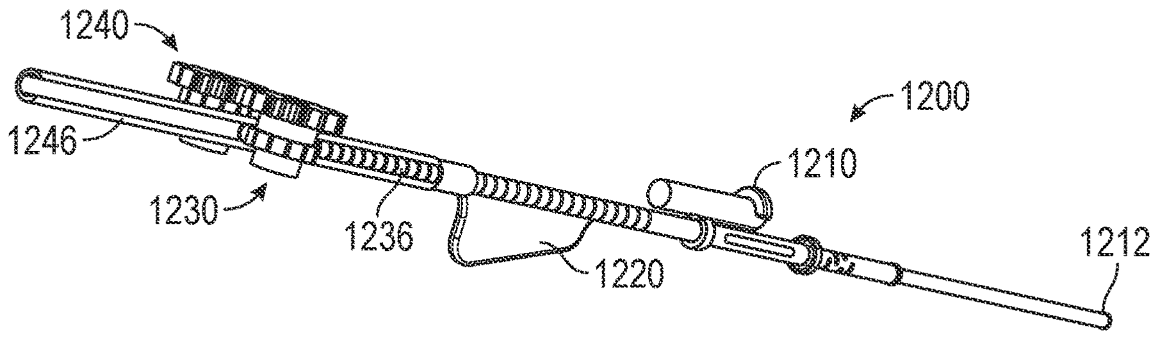
Figure 5F:
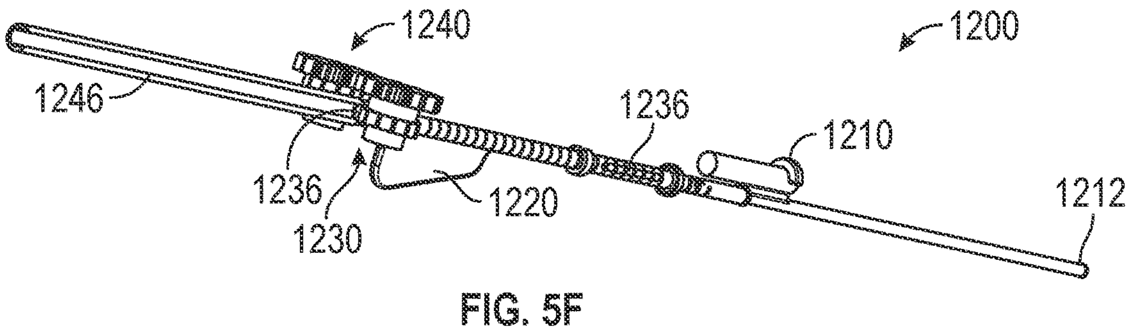
Figure 5G:
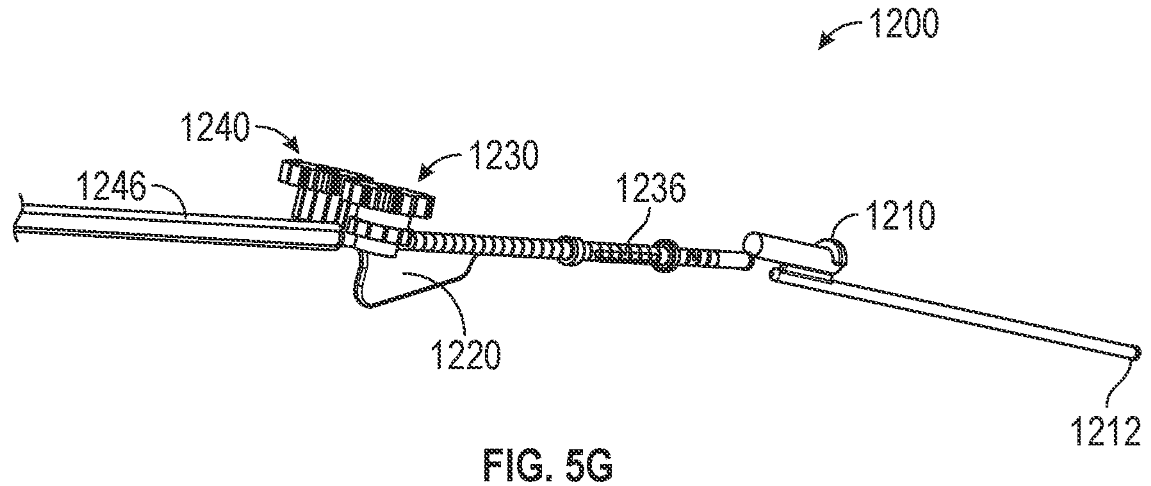
Figure 5H:
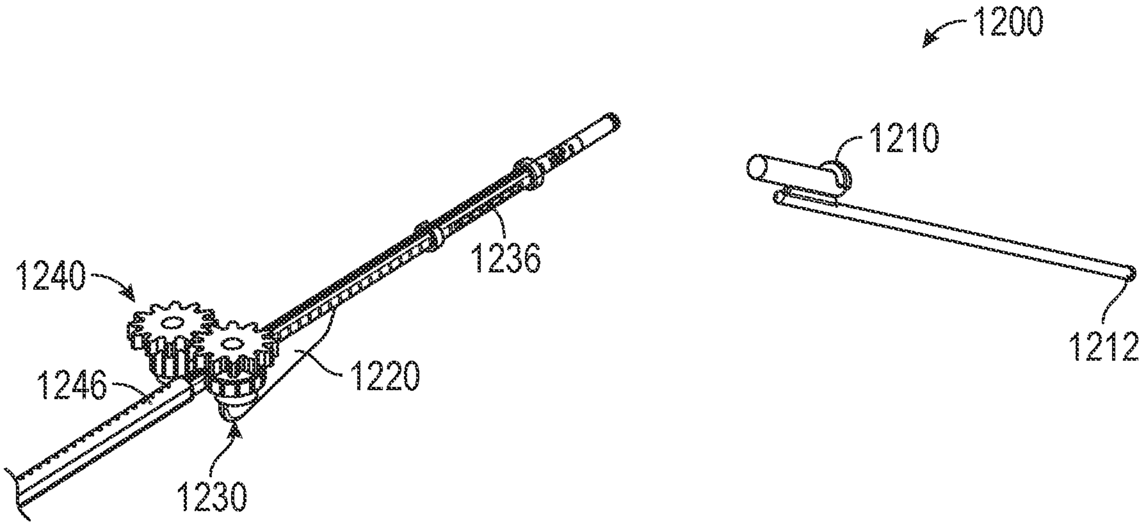

The FIGS. 5A-5H illustrate the positioning assembly 1200 operating through a range of motion of the sheath 1220 and the electrode 1210. Between FIGS. 5A and 5B relative movement of both the sheath 1220 and the electrode 1210 is illustrated, which requires coordinated activation of both the electrode pinion 1234 and the sheath drive pinion 1244. FIGS. SC-5F illustrate movement of the electrode 1210 through activation of just the electrode pinion 1234. As the electrode 1210 is advanced the distal end 1212 extends further out of the sheath 1220. FIGS. 5G to 5H illustrate detachment of the electrode 1210 from the reminder of the positioning assembly 1200.

FIGS. 6A-6G are multiple views illustrating an actuator 805 for manipulation of a perimodiolar electrode array including a sheath and electrode for use within one of the systems described above, such as system 100 or system 500. In this example, the actuator 805 includes two parallel gear racks (810, 820). One of the gear racks is the electrode gear rack 810 (also referenced as electrode actuator 810), while the other is the sheath gear rack 820 (also reference sheath actuator 820). The electrode gear rack 810 includes a gear section 812 extending from a proximal end distally over approximately ⅔rds of the length of the 810. In another example, the gear section 812 can extend further distally if additional travel is needed for a particular application. The electrode gear rack 810 also includes a dovetail groove 840 extending from the proximal end to adjacent the distal end. The dovetail groove 840 is adapted to receive a lateral end of an extension arm 824 of the sheath gear rack 820. The extension arm 824 includes a dovetail shaped lateral end that is received within the dovetail groove 840 to maintain the electrode gear rack 810 and sheath gear rack 820 in parallel to each other during operation. Similar to the electrode gear rack 810, the sheath gear rack 820 includes a gear section 822. The sheath gear rack 820 also includes a sheath holder 830 extending from adjacent the distal end of the gear section 822. The sheath holder 830 is attached to the gear section 822 via an offset 826 that aligns the sheath holder 830 with the electrode 130 as the electrode 130 will extend through the sheath 140. The sheath holder 830 also includes a forceps flange slot 832 adapted to receive a forceps flange of the sheath 140.

Figure 6A:
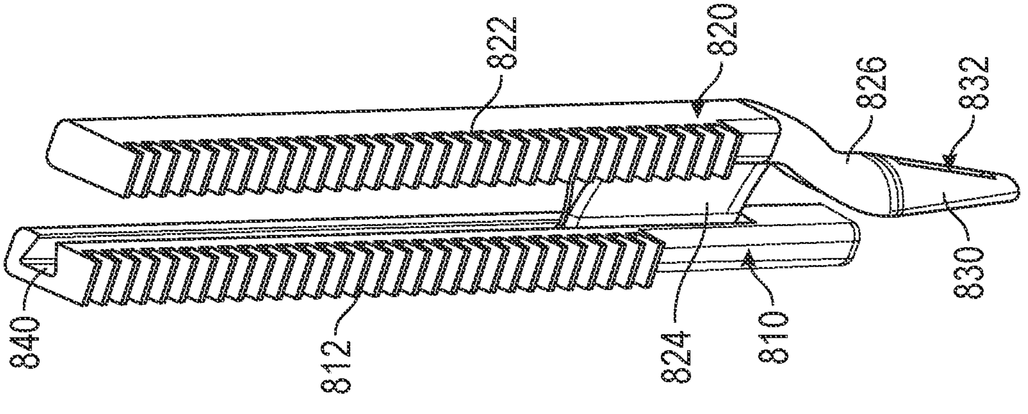
FIGS. 6A-6G are multiple views illustrating, by way of example and not limitation, an alternative actuator embodiment for manipulation of a perimodiolar electrode array including a sheath and electrode for use within one of the systems described herein.
Figure 6B:
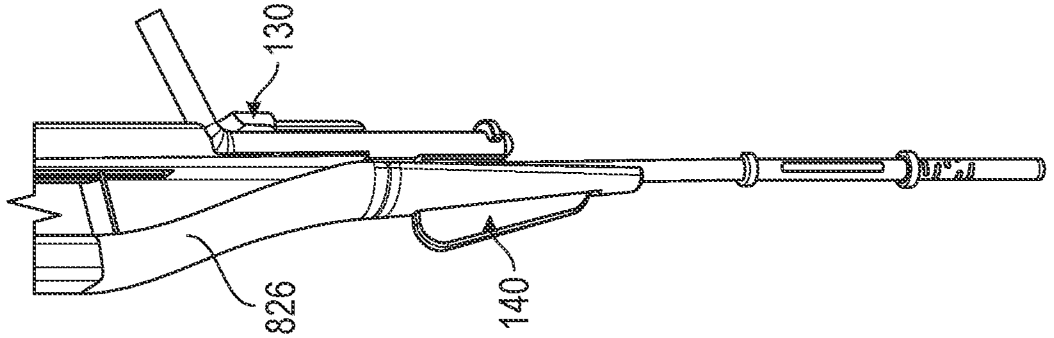
Figure 6C:
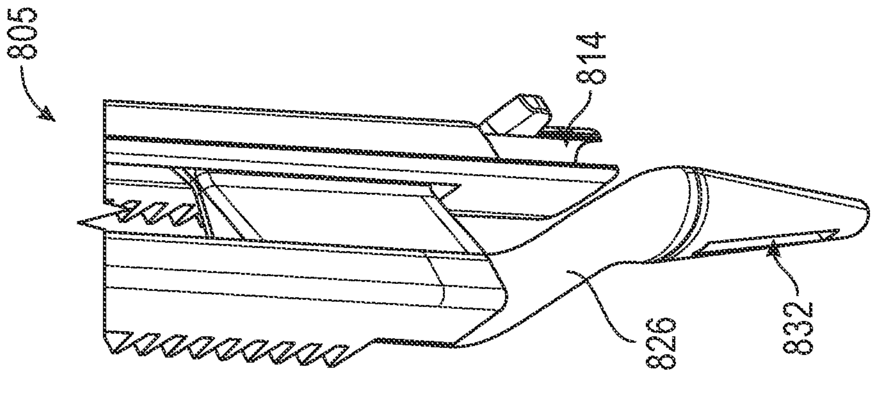
Figures 6D, 6E, 6F:
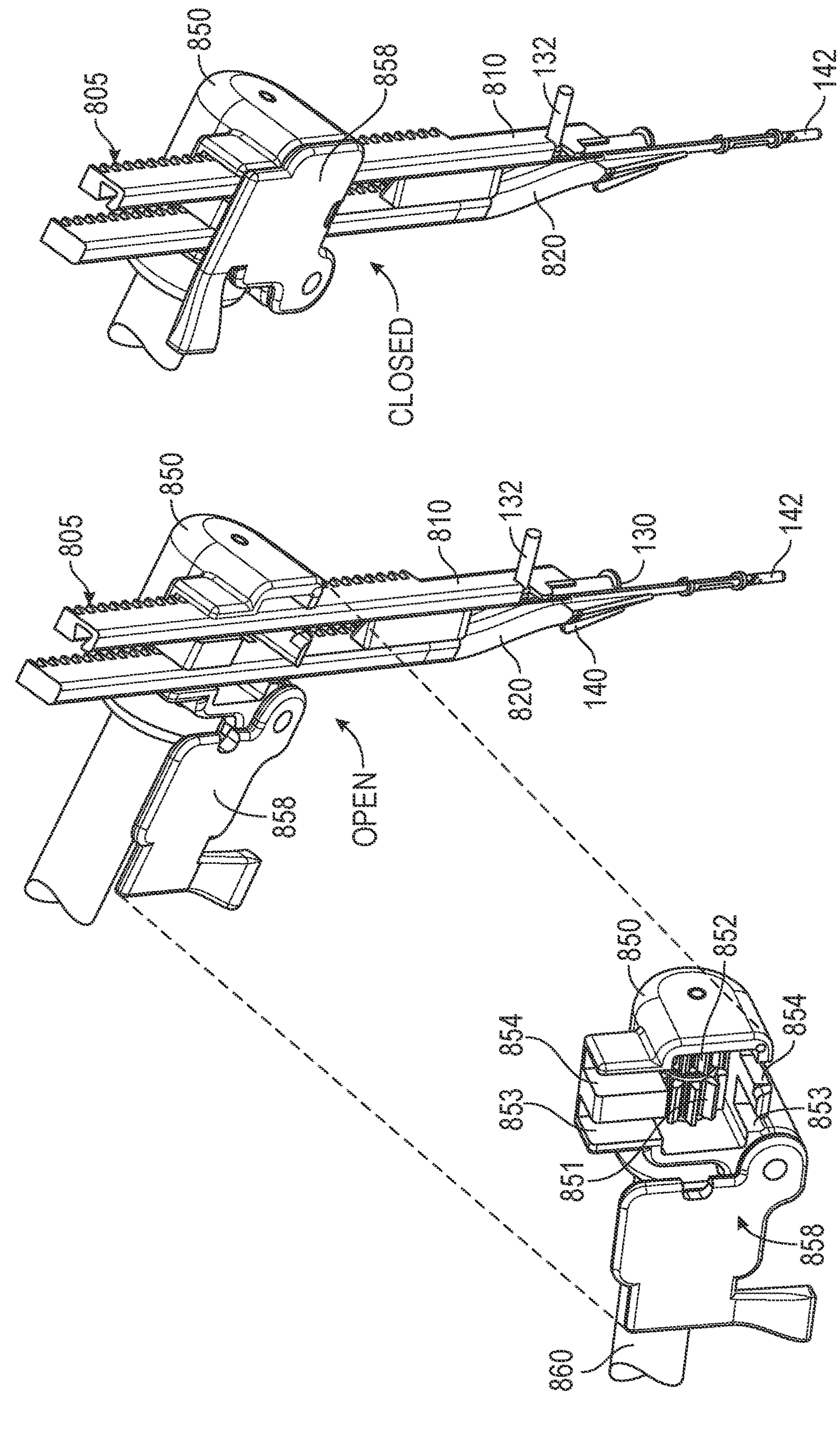

FIG. 6D illustrates a drive head 850 adapted to accept the actuator 805 discussed above. The drive head 850 includes sheath drive gear 851 and electrode drive gear 852. Extending above and below (proximal and distal of) the drive gears (851, 852), the drive head 850 includes a sheath actuator slot 853 and an electrode actuator slot 854 that are adapted to guide the sheath actuator 820 and electrode actuator 810 respectively. The drive head 850 also includes a latch door 858 that pivots over the drive head 850 to capture the actuator 805 once the electrode actuator 810 and the sheath actuator 820 are in position within the drive head 850 (see FIG. 6F where the latch door 858 is closed). The drive head 850 attaches to the remainder of the system via flexible arm 860. FIG. 6E illustrates the drive head 850 with the latch door 858 open and the actuator 805 inserted into the sheath actuator slot 853 and the electrode actuator slot 854.

Figure 6G:
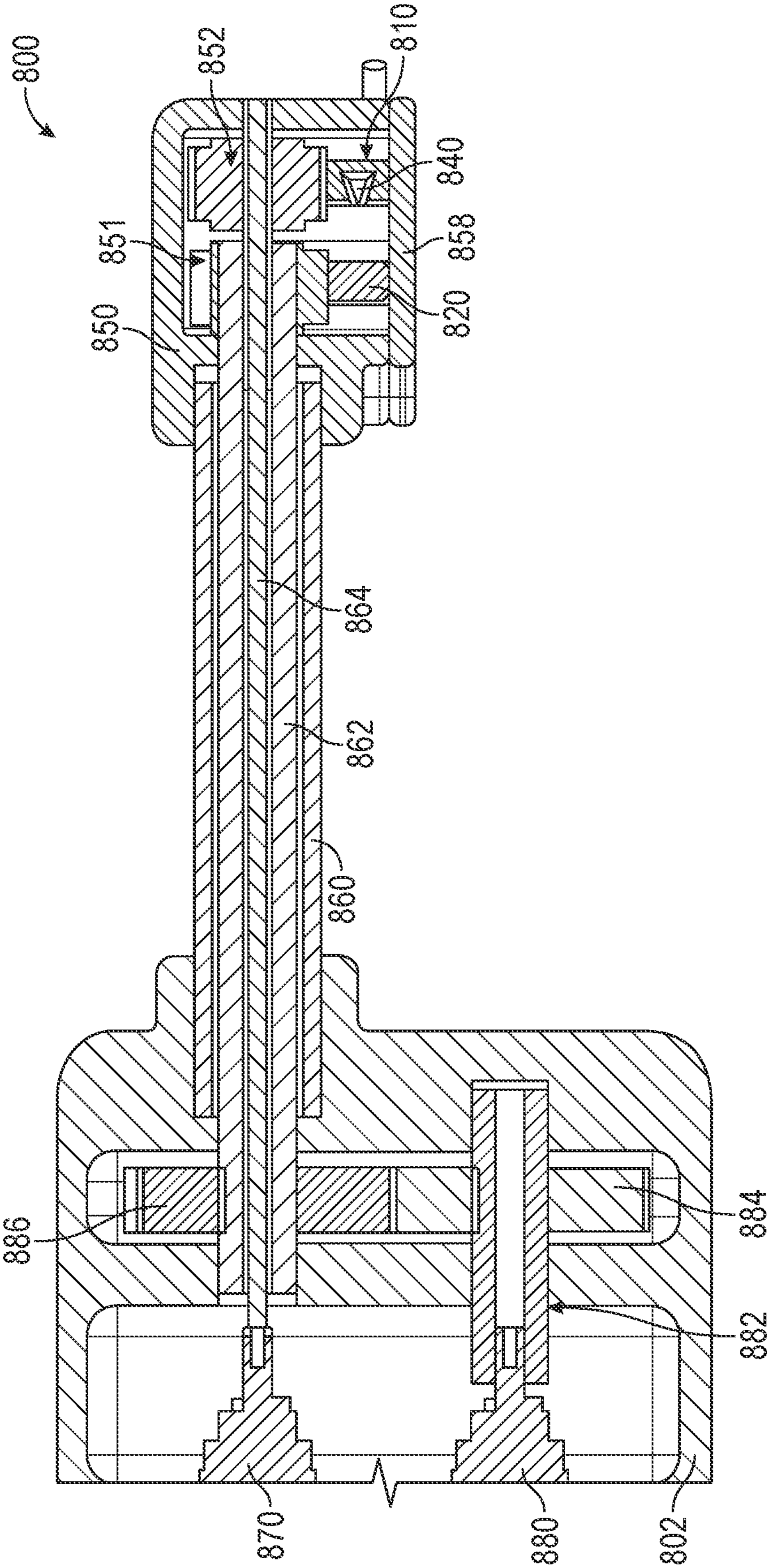

FIG. 6G is a cross-section view of the drive head 850 and additional components of an implant positioning system 800. The system 800 can include flexible arm 860, electrode motor 870, and sheath motor 880. The electrode motor 870 couples to the electrode drive gear 852 via inside drive cable 864, which extends through the outer drive cable 862 within the flexible arm 860. The outer drive cable 862 is driven by the sheath motor 880 via axle 882, a first sheath gear 884, and a second sheath gear 886. The electrode motor 870, the sheath motor 880, the first sheath gear 884 and the second sheath gear 886 are all contained with enclosure 802. A first end of the flexible arm 860 terminates within a portion of the enclosure 802.

The system 800 allows for independent manipulation of the electrode 130 and the sheath 140 within the limits of the electrode actuator 810 and the sheath actuator 820. The system 800 maintains small footprint drive head 850 that operates the actuator 805 with only two internal gears (851, 852). The system 800 enables manipulation of the sheath 140 and electrode 130 including the ability to extend the electrode 130 out of the distal end 142 of the sheath 140.

Figure 7A:
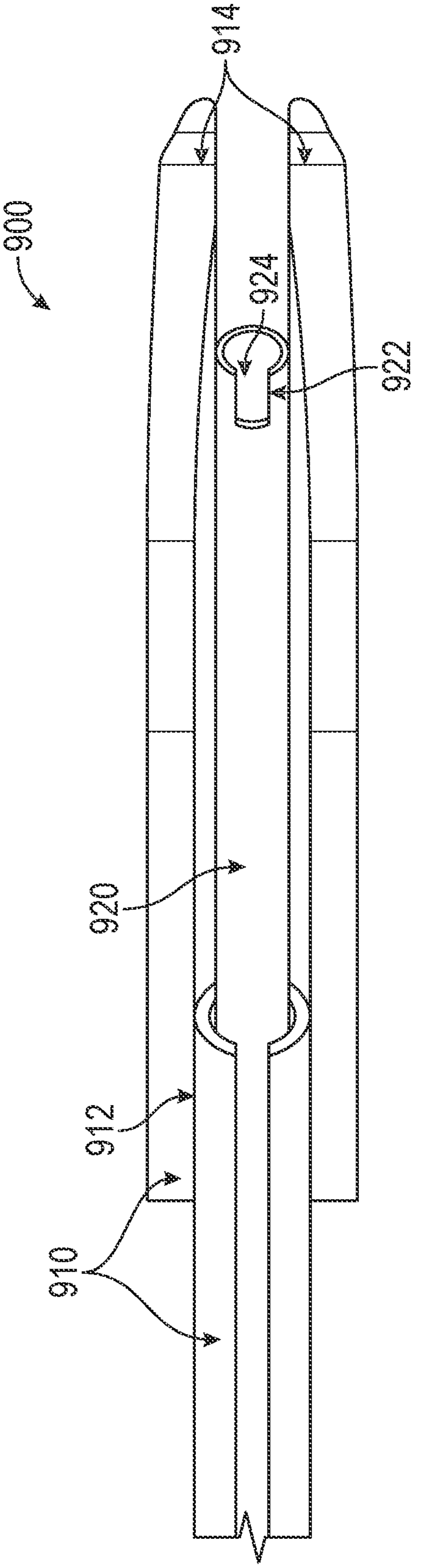
FIGS. 7A-7C are multiple views illustrating, by way of example and not limitation, another actuator embodiment for manipulation of a perimodiolar electrode array including an electrode and a sheath for use within one of the systems described herein.
Figure 7B:
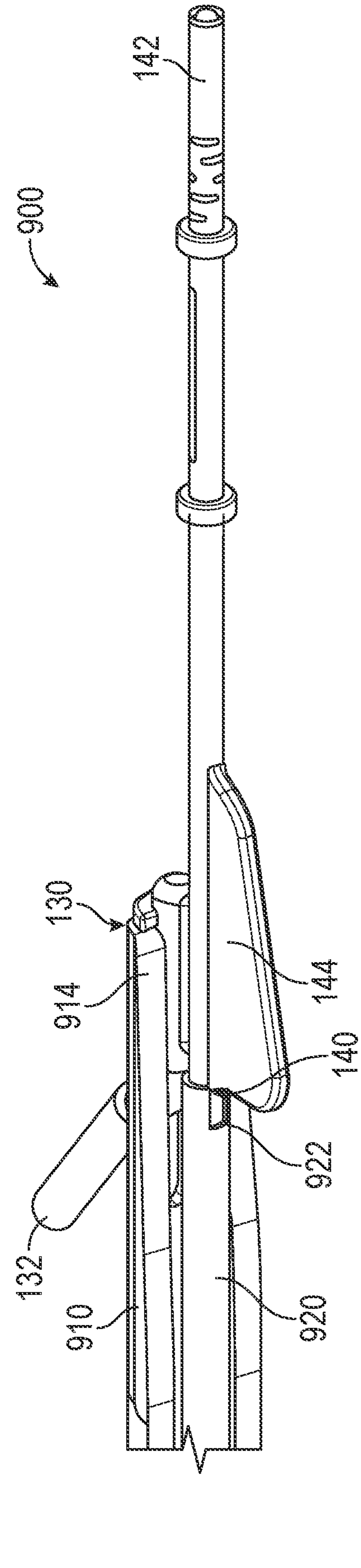
Figure 7C:
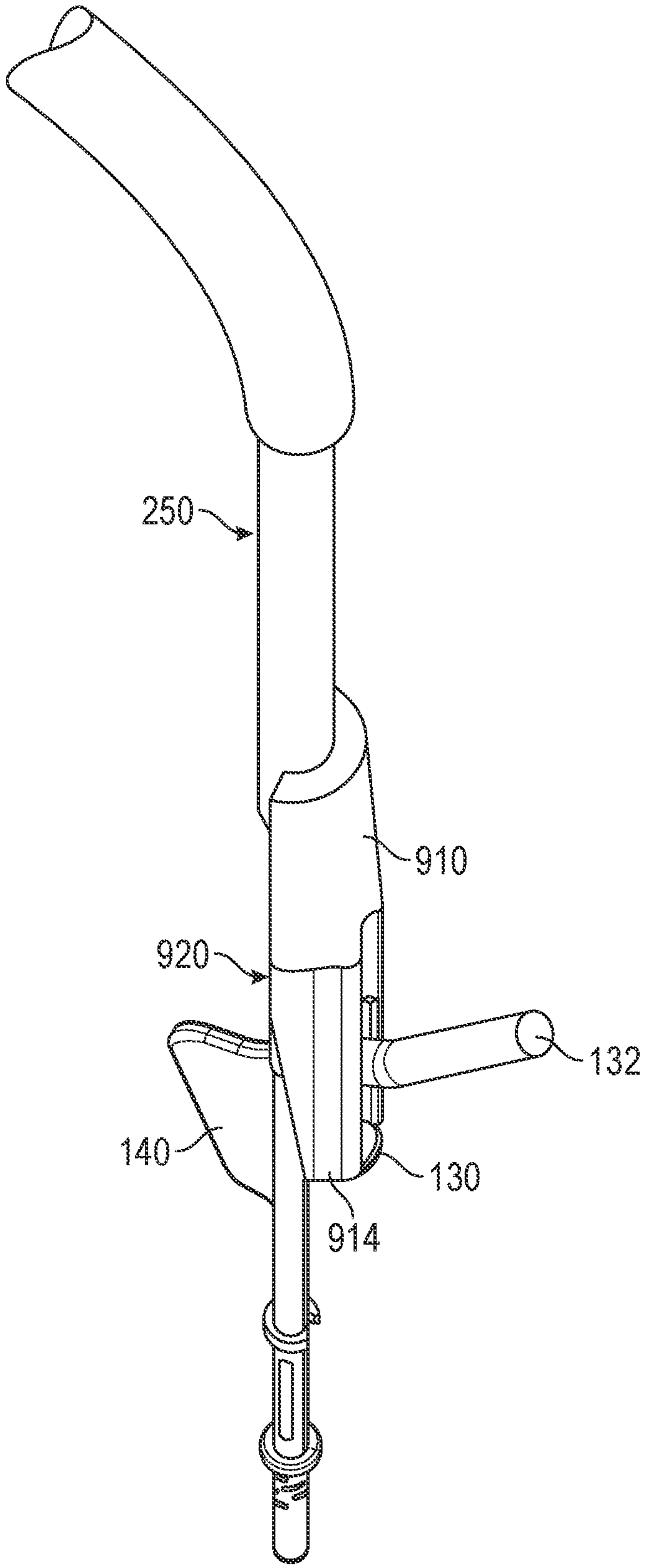

FIGS. 7A-7C are multiple views illustrating an actuator 900 for manipulation of a perimodiolar electrode array including an electrode and a sheath for use within one of the systems described above. In this example, the actuator 900 includes an electrode actuator 910 and a sheath actuator 920. The electrode actuator 910 includes a split shaft 912 and distal fingers 914. The distal fingers 914 are adapted to receive a proximal portion of the electrode 130. The distal fingers 914 include enough proximal space to allow the proximal section 132 of the electrode 130 to extend outward. The sheath actuator 920 includes a distal end 922 with a sheath grasping slot 924. As shown in FIG. 7B, the sheath grasping slot 924 is adapted to receive the forceps flange 144 of the sheath 140.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

EXAMPLES

The following are non-limiting examples of the inventive subject matter discussed herein.

Example 1 can include a system for robotically assisted manipulation of an elongate implant. In this example, the system can include a main enclosure coupled to a drive head. The main enclosure can include a first actuator to control linear movement of a sheath and second actuator to control linear movement of the elongate implant. The drive head can include a first drive structure to transmit actuation generated by the first actuator to the sheath and a second drive structure to transmit actuation generated by the second actuator to the elongate implant.

In Example 2, the subject matter of Example 1 can optionally include each of the first actuator and the second actuator having a motor rotationally coupled to a lead screw and a carriage coupled to the lead screw to translate rotation generated by the motor into linear movement.

In Example 3, the subject matter of Example 2 can optionally include each of the first actuator and the second actuator including a control cable coupled to the carriage to transmit linear movement of the carriage to the drive head.

In Example 4, the subject matter of Example 3 can optionally include the first drive structure coupling to the control cable from the first actuator to transmit linear movement to the sheath.

In Example 5, the subject matter of any one of Examples 3 and 4 can optionally include the second drive structure coupling to the control cable from the second actuator to transmit linear movement to the elongate implant.

In Example 6, the subject matter of any one of Examples 1 to 5 can optionally include the first drive structure including a rigid tube coupled to the sheath.

In Example 7, the subject matter of any one of Examples 1 to 6 can optionally include the second drive structure including a rigid tube to interface with the elongate implant.

In Example 8, the subject matter of any one of Examples 1 to 7 can optionally include the first actuator having a motor coupled to a transmission mechanism to transmit rotation to the first drive structure in the drive head.

In Example 9, the subject matter of Example 8 can optionally include the first drive structure being a friction wheel configured to transition the rotation delivered by the transmission mechanism into linear movement of the sheath.

In Example 10, the subject matter of Example 9 can optionally include the transmission mechanism including a set of gears and a torque cable.

In Example 11, the subject matter of Example 10 can optionally include the torque cable extending through a flexible gooseneck structure to the drive head.

In Example 12, the subject matter of any one of Examples 1 to 11 can optionally include the second actuator including a second motor coupled to a second transmission mechanism to transmit rotation to the second drive structure in the drive head.

In Example 13, the subject matter of Example 12 can optionally include the second drive structure being a friction wheel configured to transition the rotation delivered by the second transmission mechanism into linear movement of the elongate implant.

In Example 14, the subject matter of Example 13 can optionally include the second transmission mechanism including a central drive cable within a coaxial drive cable.

In Example 15, the subject matter of Example 14 can optionally include the coaxial drive cable including an outer drive cable coupled to the first actuator.

In Example 16, the subject matter of any one of Examples 1 to 15 can optionally include the first drive structure including a drive wheel to transmit rotation to a sheath actuator.

In Example 17, the subject matter of Example 16 can optionally include the sheath actuator including a cylindrical tube with a proximal half cylinder section and a distal end couplable to the sheath.

In Example 18, the subject matter of any one of Examples 1 to 17 can optionally include the second drive structure including a drive wheel to transmit rotation to an elongate implant actuator.

In Example 19, the subject matter of Example 18 can optionally include the elongate implant actuator being a cylindrical structure that extends through an open side wall of a cylindrical sheath actuator.

In Example 20, the subject matter of any one of Examples 1 to 19 can optionally include each of the first actuator and the second actuator including a linear electric motor or a linear actuator to generate the linear movement.

In Example 21, the subject matter of any one of Examples 1 to 20 can optionally include a gooseneck extending out of the enclosure to transmit actuation generated by the first actuator and the second actuator to the sheath and the elongate implant via the drive head.

Example 22 is a system including a first motor, a second motor, a first transmission mechanism, a second transmission mechanism, a first actuation mechanism, and a second actuator mechanism. The first transmission mechanism is coupled to the first motor, and the second transmission mechanism is coupled to the second motor. The first actuation mechanism is coupled to the first transmission mechanism to transmit movement generated by the first motor to a sheath actuator. The second actuation mechanism is coupled to the second transmission mechanism to transmit movement generated by the second motor to an electrode actuator.

In Example 23, the subject matter of Example 22 can optionally include the first actuation mechanism having a first drive wheel driven by one or more gears, the one or more gears driven by a torque cable coupled to the first motor.

In Example 24, the subject matter of Example 23 can optionally include the drive wheel including a pinion gear configured to engage a sheath rack portion of the sheath actuator.

In Example 25, the subject matter of any one of Examples 22 to 24 can optionally include the second actuation mechanism includes a second drive wheel driven by a torque cable coupled to the second motor.

In Example 26, the subject matter of Example 25 can optionally include the second drive wheel including a pinion gear configured to engage an electrode rack portion of the electrode actuator.

In Example 27, the subject matter of any one of Examples 22 to 26 can optionally include the first actuation mechanism having a sheath gear including gear teeth adapted to engage a gear section of the sheath actuator.

In Example 28, the subject matter of any one of Examples 22 to 27 can optionally include the second actuation mechanism including an electrode gear including gear teeth adapted to engage a gear section of the electrode actuator.

In Example 29, the subject matter of any one of Examples 22 to 28 can optionally include the electrode actuator including a dovetail groove extending from a proximal end to a distal position adjacent a distal end of the electrode actuator.

In Example 30, the subject matter of Example 29 can optionally include the sheath actuator including a lateral extension arm including a dovetail shaped lateral end, the dovetailed shaped lateral end received within the dovetail groove.

In Example 31, the subject matter of Example 30 can optionally include the dovetail groove and the dovetailed shaped lateral end operable to enable restrained relative linear movement between the electrode actuator and the sheath actuator while maintaining parallel orientation between the electrode actuator and the sheath actuator.

In Example 32, the subject matter of any one of Examples 22 to 31 can optionally include the sheath actuator including an offset distal section extending into a distal end including a forceps flange slot adapted to receive a portion of the sheath.

In Example 33, the subject matter of any one of Examples 22 to 32 can optionally include the electrode actuator including distal fingers to engage an electrode.

In Example 34, the subject matter of Example 33 can optionally include the sheath actuator extending from a split shaft portion of the electrode actuator and includes a forceps flange slot on a distal end.

What is claimed is:

1. A system for robotically assisted manipulation of an elongate implant, the system comprising:

a main enclosure housing a first actuator to control linear movement of a sheath and second actuator to control linear movement of the elongate implant; and a drive head including a first drive structure to transmit actuation generated by the first actuator to the sheath and a second drive structure to transmit actuation generated by the second actuator to the elongate implant; wherein each of the first actuator and the second actuator include a motor rotationally coupled to a lead screw and a carriage coupled to the lead screw to translate rotation generated by the motor into linear movement.

2. The system of claim 1, wherein each of the first actuator and the second actuator further include a control cable coupled to the carriage to transmit linear movement of the carriage to the drive head.

3. The system of claim 2, wherein the first drive structure couples to the control cable from the first actuator to transmit linear movement to the sheath.

4. The system of claim 2, wherein the second drive structure couples to the control cable from the second actuator to transmit linear movement to the elongate implant.

5. The system of claim 1, wherein the first actuator includes a motor coupled to a transmission mechanism to transmit rotation to the first drive structure in the drive head.

6. The system of claim 5, wherein the first drive structure is a friction wheel configured to transition the rotation delivered by the transmission mechanism into linear movement of the sheath.

7. The system of claim 6, wherein the transmission mechanism includes a set of gears and a torque cable.

8. The system of claim 7, wherein the torque cable extends through a flexible gooseneck structure to the drive head.

9. The system of claim 1, wherein the second actuator includes a second motor coupled to a second transmission mechanism to transmit rotation to the second drive structure in the drive head.

10. The system of claim 9, wherein the second drive structure is a friction wheel configured to transition the rotation delivered by the second transmission mechanism into linear movement of the elongate implant.

11. The system of claim 10, wherein the second transmission mechanism includes a central drive cable within a coaxial drive cable.

12. The system of claim 11, wherein the coaxial drive cable includes an outer drive cable coupled to the first actuator.

13. The system of claim 1, wherein the first drive structure includes a drive wheel to transmit rotation to a sheath actuator, and wherein the sheath actuator includes a cylindrical tube with a proximal half cylinder section and a distal end couplable to the sheath.

14. The system of claim 1, wherein the second drive structure includes a drive wheel to transmit rotation to an elongate implant actuator, and wherein the elongate implant actuator is a cylindrical structure that extends through an open side wall of a cylindrical sheath actuator.

15. The system of claim 1, further comprising a gooseneck extending out of the enclosure to transmit actuation generated by the first actuator and the second actuator to the sheath and the elongate implant via the drive head.

* * * * *